(12) United States Patent
Kwon et al.

(10) Patent No.: US 11,291,722 B2
(45) Date of Patent: Apr. 5, 2022

(54) VACCINE COMPOSITION COMPRISING CYCLIC PEPTIDES, ANTIBODIES TO THE CYCLIC PEPTIDES OR AN ANTICANCER COMPOSITION COMPRISING THE SAME

(71) Applicant: Industry Academic Cooperation Foundation, Hallym University, Chuncheon-si (KR)

(72) Inventors: Hyung Joo Kwon, Cheongju-si (KR); Yong Sung Kim, Suwon-si (KR)

(73) Assignee: INDUSTRY ACADEMIC COOPERATION FOUNDATION HALLYM UNIVERSITY, Chuncheon-si (KR)

( * ) Notice: Subject to any disclaimer, the term of this patent is extended or adjusted under 35 U.S.C. 154(b) by 188 days.

(21) Appl. No.: 16/313,695

(22) PCT Filed: Jul. 11, 2017

(86) PCT No.: PCT/KR2017/007407
§ 371 (c)(1),
(2) Date: Dec. 27, 2018

(87) PCT Pub. No.: WO2018/034434
PCT Pub. Date: Feb. 22, 2018

(65) Prior Publication Data
US 2019/0231872 A1 Aug. 1, 2019

(30) Foreign Application Priority Data
Aug. 17, 2016 (KR) .................. 10-2016-0104343

(51) Int. Cl.
| | |
|---|---|
| *A61K 39/39* | (2006.01) |
| *A61K 39/395* | (2006.01) |
| *G01N 33/574* | (2006.01) |
| *C07K 16/18* | (2006.01) |
| *A61P 35/04* | (2006.01) |
| *A61K 39/00* | (2006.01) |
| *A61K 9/127* | (2006.01) |
| *C07K 16/28* | (2006.01) |

(52) U.S. Cl.
CPC .......... *A61K 39/3955* (2013.01); *A61K 9/127* (2013.01); *A61K 39/001102* (2018.08); *A61K 39/395* (2013.01); *A61P 35/04* (2018.01); *C07K 16/18* (2013.01); *C07K 16/28* (2013.01); *G01N 33/574* (2013.01); *G01N 33/57492* (2013.01); *A61K 2039/505* (2013.01); *A61K 2039/55561* (2013.01); *A61K 2039/572* (2013.01); *C07K 2317/24* (2013.01); *C07K 2317/565* (2013.01); *C07K 2317/73* (2013.01); *C07K 2317/92* (2013.01); *G01N 2333/705* (2013.01)

(58) Field of Classification Search
None
See application file for complete search history.

(56) References Cited

U.S. PATENT DOCUMENTS

2015/0239975 A1* 8/2015 Kim .................. G01N 33/577
424/143.1

OTHER PUBLICATIONS

Hyung-Joo Kwon, et al.,Prevention and Therapy of Hepatocellular Carcinoma by Vaccination with TM4SF5 Epitope-CpG-DNA-Liposome omplex without Carriers, PLoS ONE. 2012, Mar. 2012 | vol. 7 | Issue 3:e33121.

* cited by examiner

*Primary Examiner* — Nelson B Moseley, II

(57) ABSTRACT

The present invention relates to a vaccine composition comprising cyclic peptides of the present invention, antibodies to cyclic peptides, or an anticancer composition comprising them, and the vaccine composition of the present invention exhibit an inhibitory activity for metastasis of cancer. In addition, the antibodies of the present invention bind to the tumor-specific antigen TM4SF5 with high affinity, and significantly inhibit the growth, metastasis and invasion of cancer cells expressing the tumor-specific antigen TM4SF5, and thus can be used for diagnosis, prevention or treatment of various cancers expressing TM4SF5.

3 Claims, 16 Drawing Sheets

Specification includes a Sequence Listing.

| TM4SF5 target region sequence | $^{131}$TAGAYLLNRTLWDRCEAPPRVVPWNVT$^{157}$ |
|---|---|

B

| Abbreviations | Peptide sequences |
|---|---|
| hTM4SF5EC2-C | $^{131}$TACAYLLNRTLWDRCEAPPRVVPWNCT$^{157}$ |
| mTM4SF5EC2-C | $^{130}$TECAYLRNDTLWNLCEAPPHVVPWNCT$^{156}$ |
| hTM4SF5EC2 | $^{131}$TACAYLLNRTLWDRCEAPPRVVPWNCT$^{157}$ |
| mTM4SF5EC2 | $^{130}$TECAYLRNDTLWNLCEAPPHVVPWNCT$^{156}$ |
| hTM4SF5R2-3 | $^{138}$NRTLWDRCEAPPRV$^{151}$ |
| mTM4SF5R2-3 | $^{137}$NDTLWNLCEAPPHV$^{150}$ |

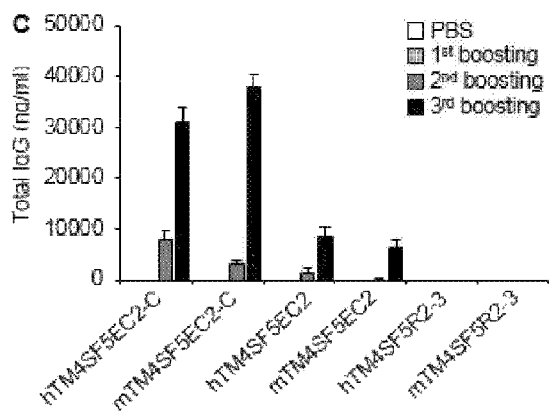

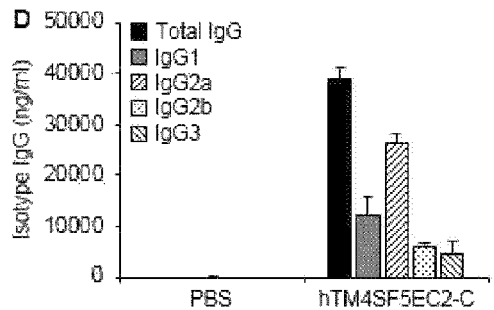

[Figure 2]
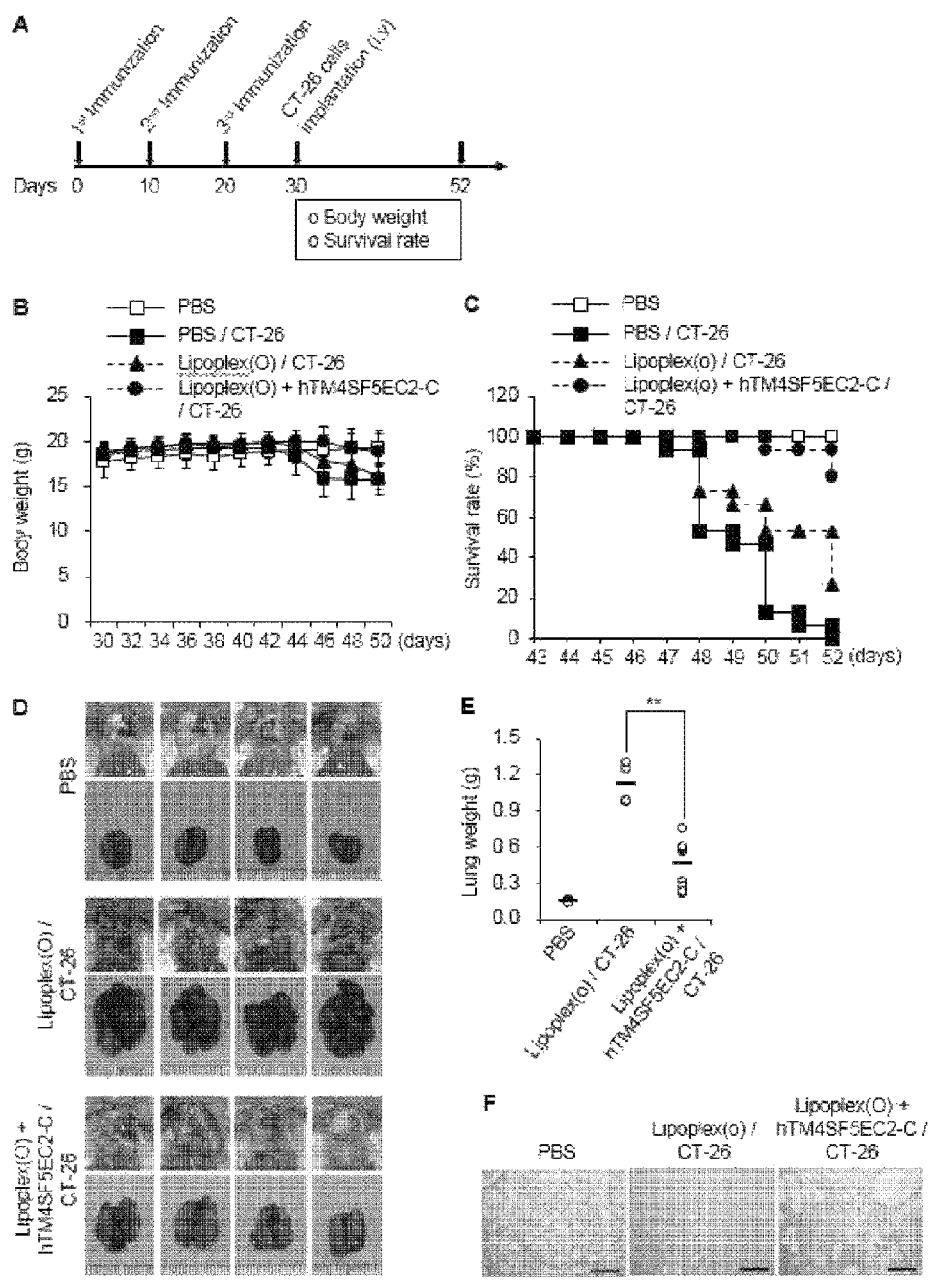

[Figure 3]
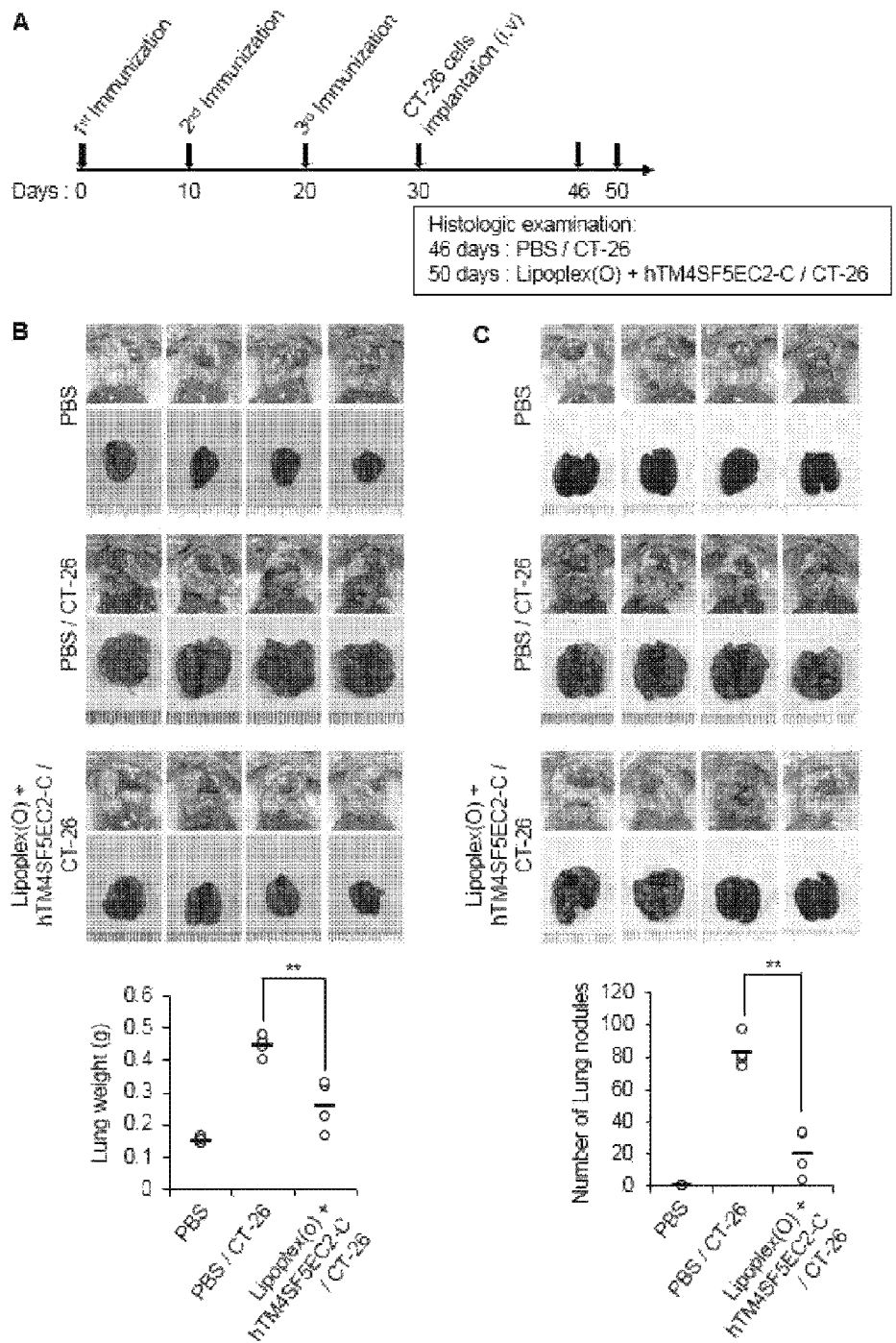

[Figure 4]
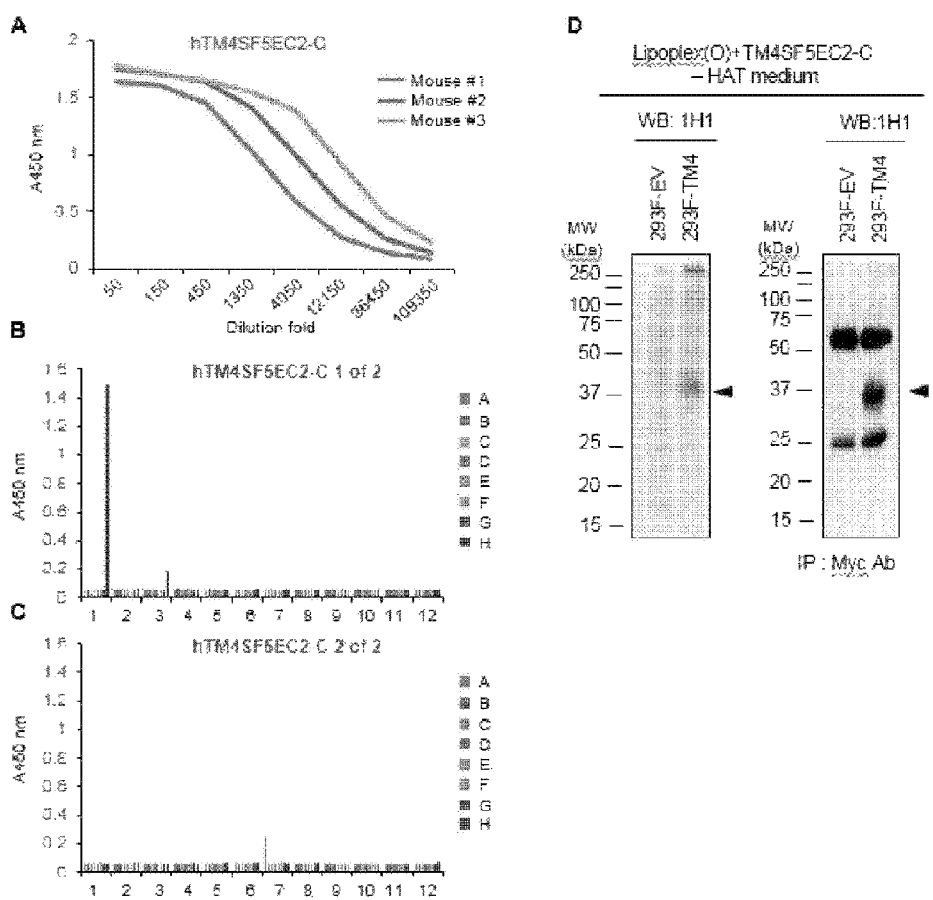

[Figure 5]
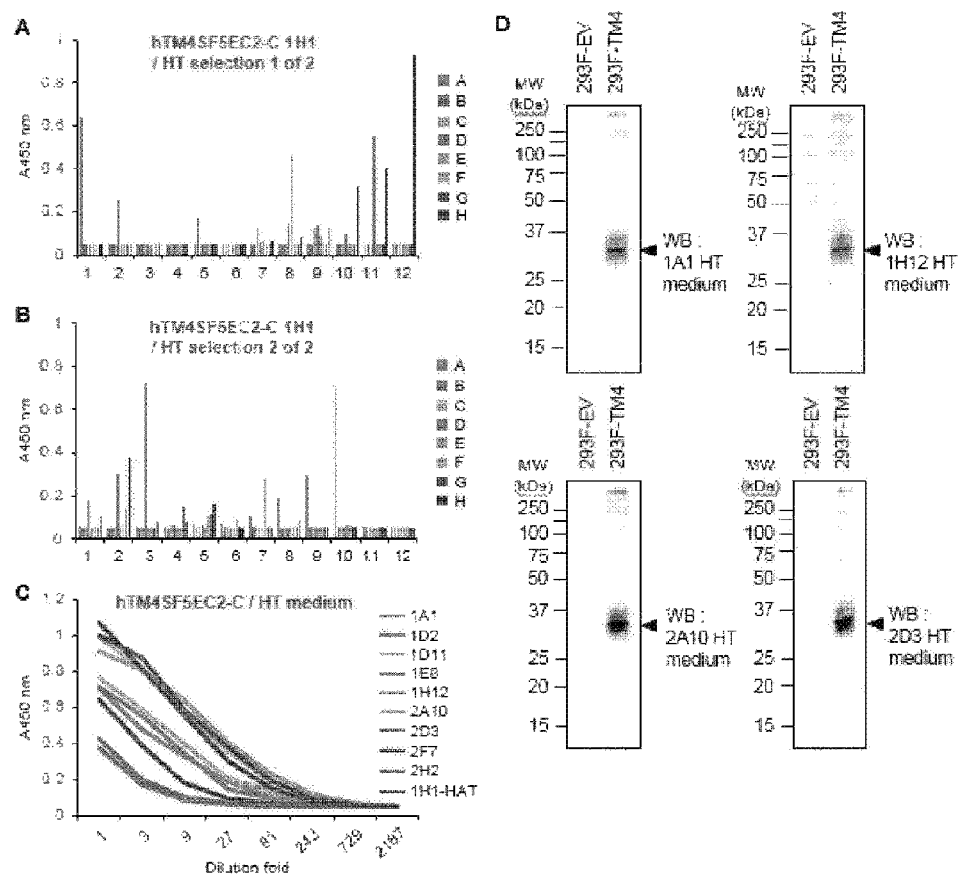

[Figure 6]
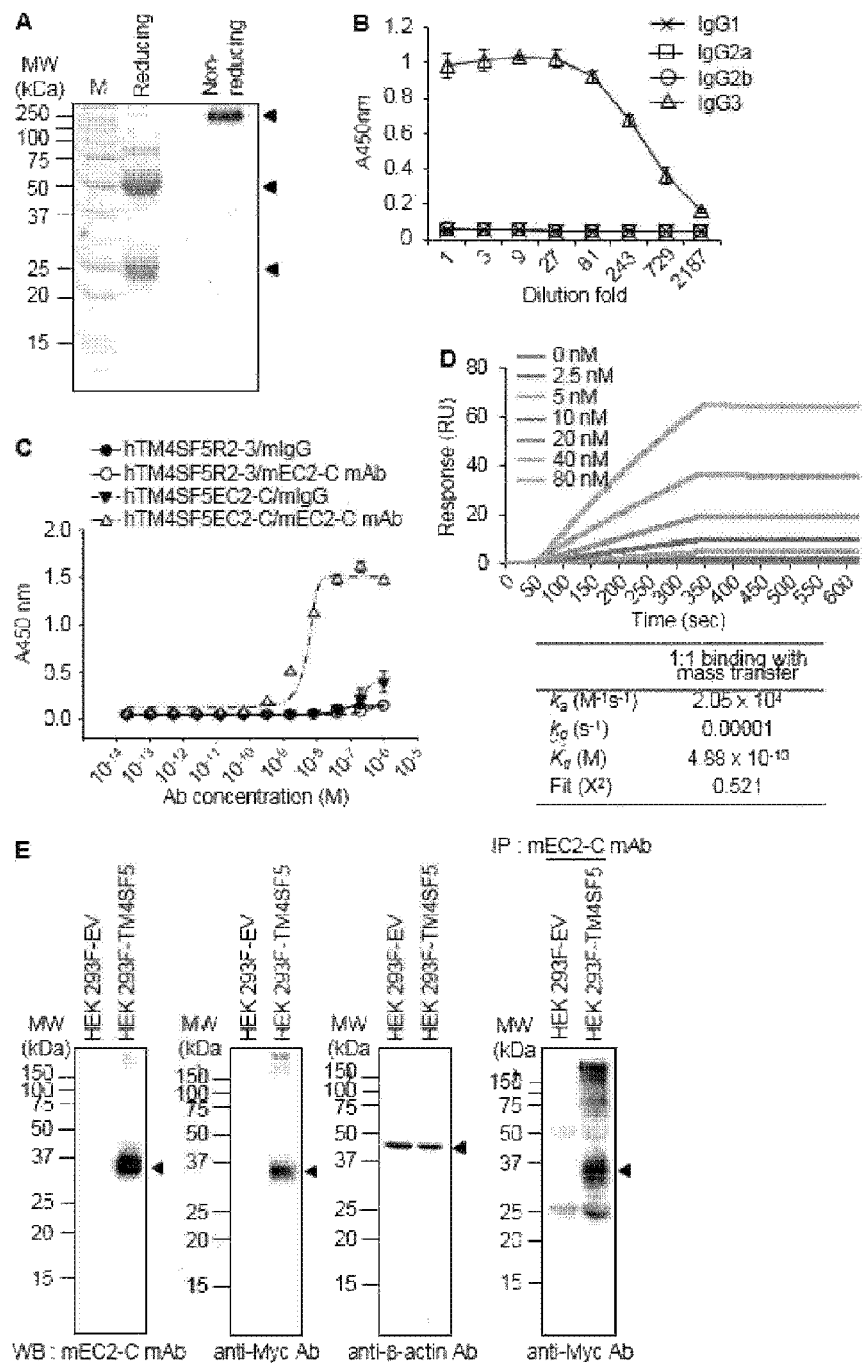

[Figure 7]
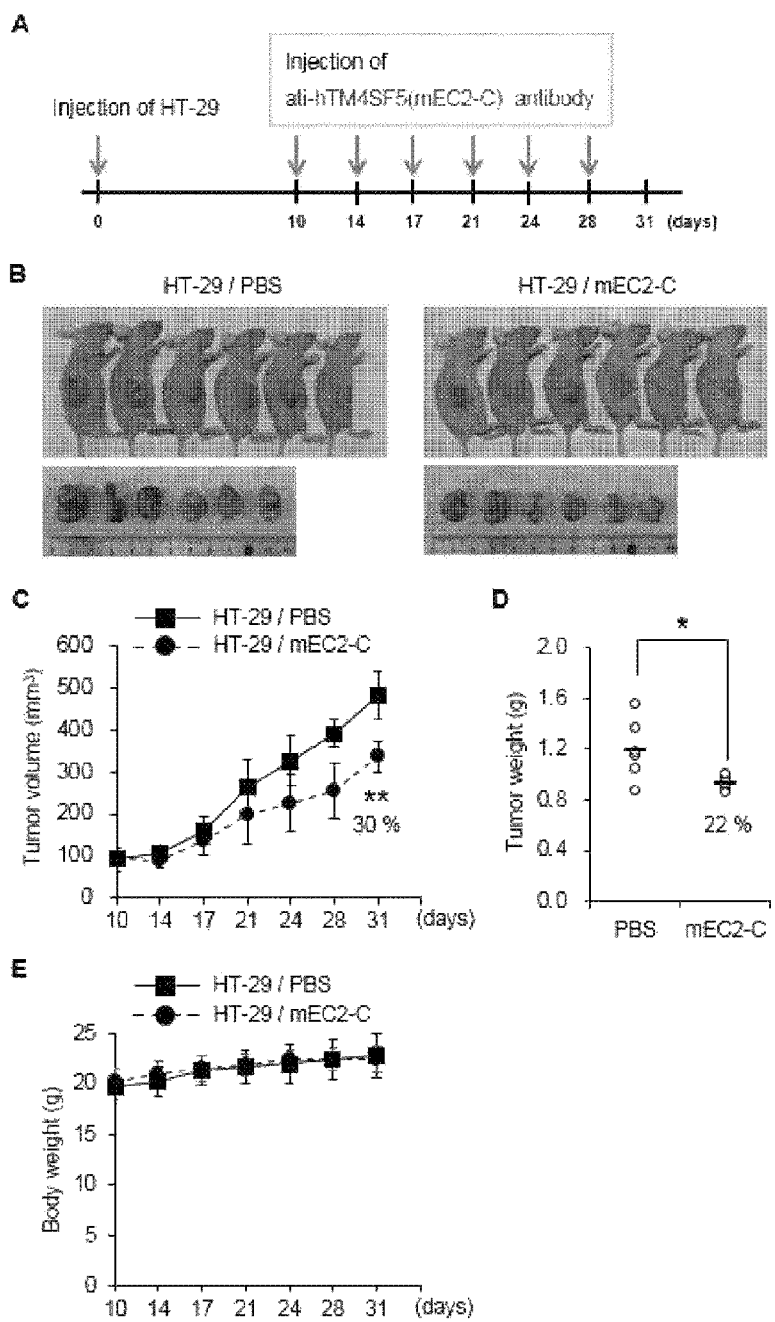

Heavy chain

CTTCCG GAATTC
CAGGTTCAGCTGGAGGAGTCAGGACCTGGCCTGGTGGCGCCCTCACAGAGCCTGTCCATCATATGCACTGTCTCAGGATTCTCCTTA
ACCAGCTATGGTGTAACCTGGGTTCGCCAGCCTCCAGGAAAGGGTCTGGAGTGGCTGGGAGTAATATGGAGTGACGGCAGCACAAAT
TATCAGTCAGCTCTCATATCCAGACTGACCATCAGCAGGGATAACTCCAAGAGCCAAGCTTTCTTAAAACTGAACAGTCTGCAAACT
GATGACACAGCCACGTACTACTGTGCCAGACCTAGTAACTACTACTACTTTGACTACTGGGGCCAAGGCACCACTCTCACAGTCTCC
TCAGCTACAACAACAGCCCCATCTGTCTATCCCTTGGTCCCT AGATCT TCC

```
                            CDR1                       CDR2
kabat                    <------>              <--------------->
AbM                      <-------->            <-------->
Chothia                  <------>              <---->
         QVQLEESGPGLVAPSQSLSIICTVSGFSLISYGVTWVRQPPGKGLEWLGVIWSDGSTNYQSALISRLIISRDNSKSQ CDR3
kabat    <-------->
AbM      <-------->
Chothia  <-------->
         AFLKLNSLQTDDTATYYCARPSNYYFDYWGQGTTLTVSSAITTAPSVYPLVPRSS
```

B

Light chain

GC GAGCTC
GATATTGTGATGACACAGTCTCCATCCTCCCTGGCTGTGTCAGCAGGAGAGAGGGTCACTTTGAGCTGCAAATCCAGTCAGAGTCTG
TTCGACAGAAGAACCCGAAGACCTACTTGGCTTGGTACCAGCAGAAACCAGGGCAGTCTCCTAAACTGCTGATCTCCTGGGCATCC
ACTAGGGAATCTGGGGTCCCTGATCGCTTCACAGGCAGTGGATCTGGACAGATTTCACTCTCACCATCAGCAGTGTGCAGGCTGAA
GACCTGGCAGTTTATTATTGCAAACAATCTTATAATCTGTTCACGTTCGGAGGGGGGACCAAGCTGGAAATAAAACGGGCTGATGCT
GCACCAACTGTATCC GCATGC ACC

```
                      CDR1                     CDR2
             <-------------->              <----->
DIVMTQSPSSLAVSAGERVTLSCKSSQSLFDRPTRKTYLAWYQQKPGQSPKLLISWASTRESGVPDRFTGSGSG

CDR3
         <-------->
TDFTLTISSVQAEDLAVYYCKQSYNLFTFGGGTKLEIKRADAAPTVSACT
```

```
              10         20         30           40          50         60
mEC2-C     QVQLEESGPGLVAPSQSLSIICTVSGFSL [TSYGVT] WVRQPPGKGLEWLG [VIWSDGSTNYQ
hVH3       EVQLVESGGGLVQPGGSLRLSCAASGFNI [KSNYMS] WVRQAPGKGLEWVS [VIYSGGSTYYA
hEC2-C-1   EVQLVESGGGLVQPGGSLRLSCAASGFNI [TSYGVT] WVRQAPGKGLEWVA [VIWSDGSTNYQ
hEC2-C-2   EVQLVESGGGLVQPGGSLRLSCAASGFSL [TSYGVT] WVRQAPGKGLEWLG [VIWSDGSTNYQ
                                       **    *                    **

70       80  abc   90         100   a      110
mEC2-C     SALIS] RLTISRDNSKSQAFLKLNSLQTDDTATYYCAR [PSNYYF--DY] WGQGTTLTVSS
hVH3       DSVKG] RFTISADTSKNIAYLQMNSLRAEDTAVYYCSR [WGGDGFYAMDY] WGQGTLVTVSS
hEC2-C-1   SALIS] RFTISADTSKNIAYLQMNSLRAEDTAVYYCSR [PSNYYF--DY] WGQGTLVTVSS
hEC2-C-2   SALIS] RLTISRDNSKNIAYLQMNSLRAEDTAVYYCAR [PSNYYF--DY] WGQGTLVTVSS
                  *   * *                         *
```

VL

```
              10         20    abcdef 30         40          50
mEC2-C     DIVMTQSPSSLAVSAGERVTLSC [KSSQSLFDRBTRKTYLA] WYQQKPGQSPKLLIS [WA
hVk1       DIQMTQSPSSLSASVGDRVTITC [RASQ------SISSYLN] WYQQKPGKAPKLLIY [AA
hEC2-C-1   DIQMTQSPSSLSASVGDRVTITC [KSSQSLFDRBTRKTYLA] WYQQKPGKAPKLLIY [WA
hEC2-C-2   DIQMTQSPSSLSASVGDRVTITC [KSSQSLFDRBTRKTYLA] WYQQKPGKAPKLLIS [WA
                                                                   *

60         70       80         90         100
mEC2-C     STRES] GVPDRFTGSGSGTDFTLTISSVQAEDLAVYYC [KQSYN-LFT] FGGGTKLEIKR
hVk1       SSLQS] GVPSRFSGSRSGTDFTLTISSLQPEDFATYYC [QQSYSTPFT] FGGGTKLEIKR
hEC2-C-1   STRES] GVPSRFSGSRSGTDFTLTISSLQPEDFATYYC [KQSYN-LFT] FGQGTKVEIKR
hEC2-C-2   STRES] GVPSRFSGSGSGTDFTLTISSLQPEDFATYYC [KQSYN-LFT] FGQGTKVEIKR
                           *
```

【Figure 10】
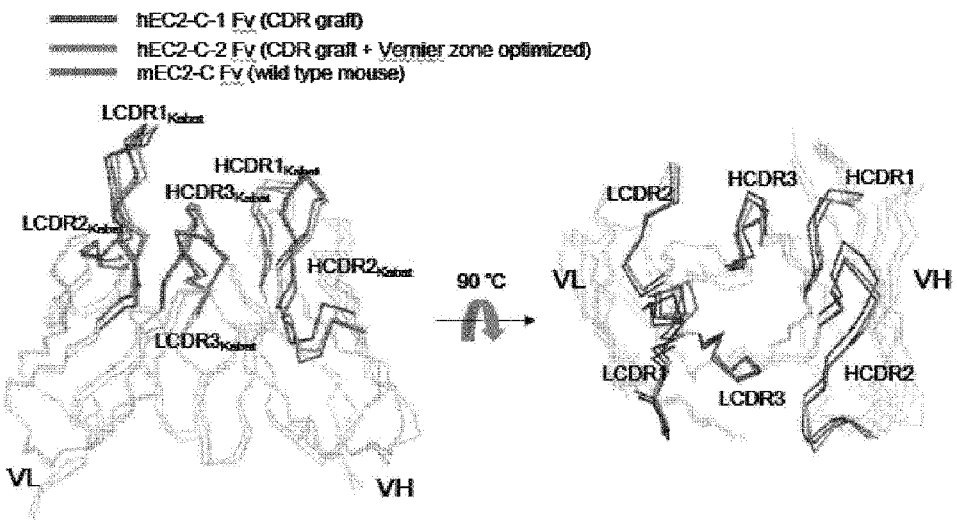
【Figure 11】
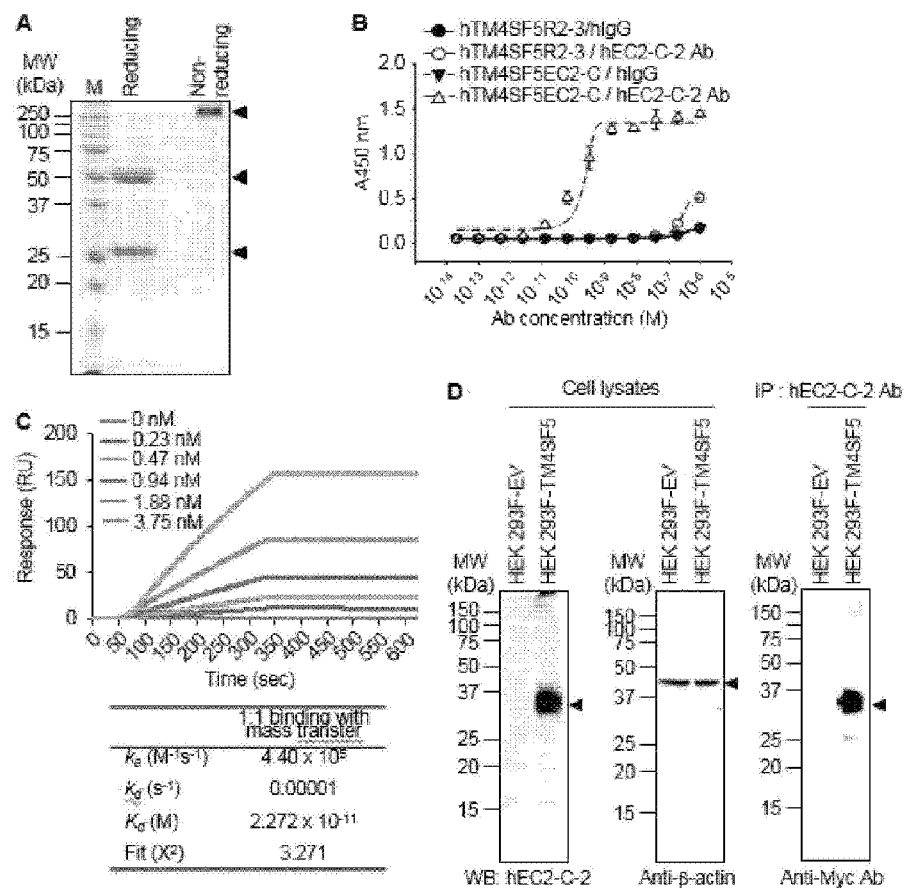

[Figure 12]
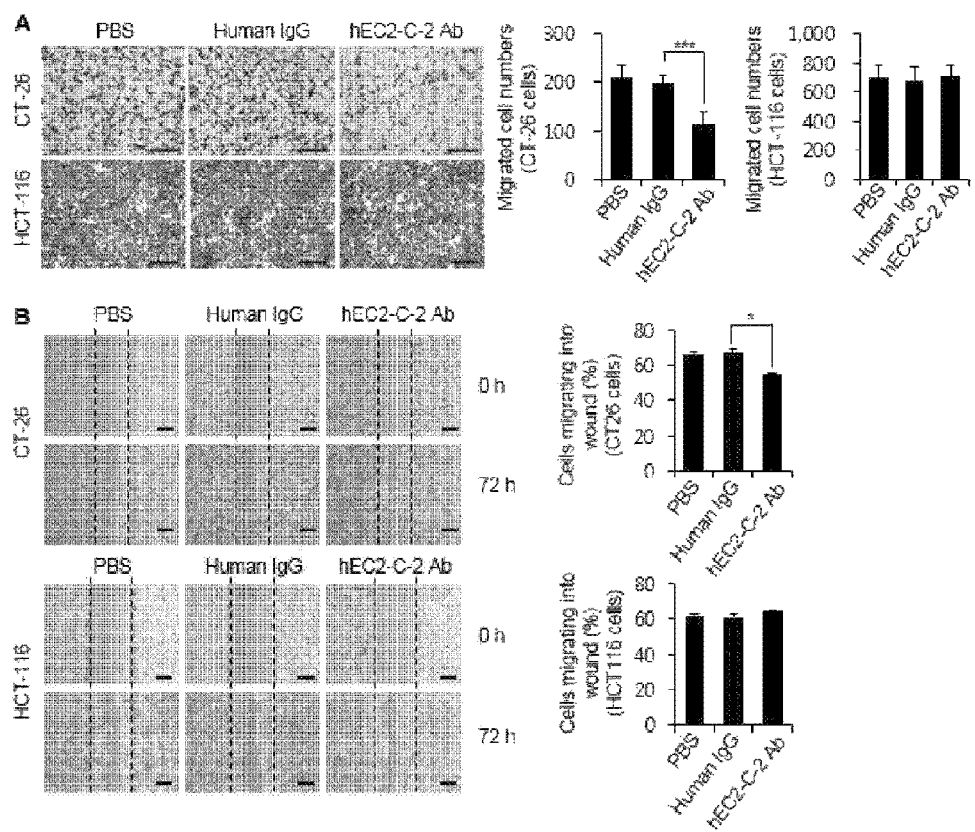

【Figure 13】
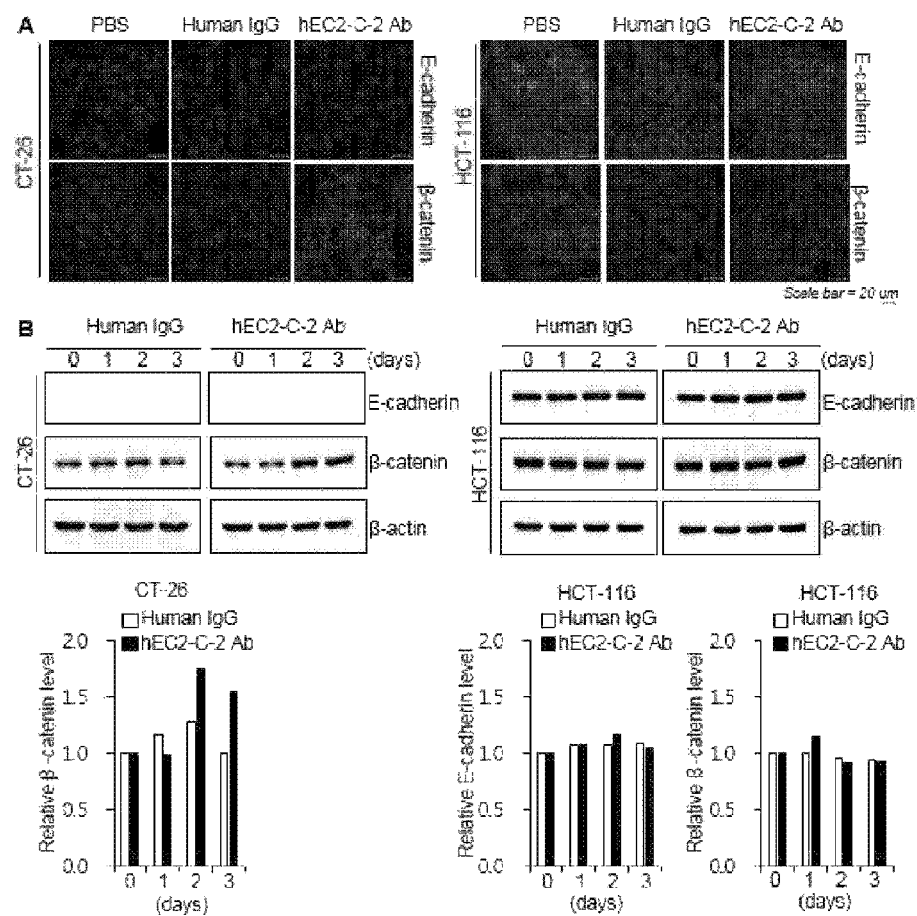

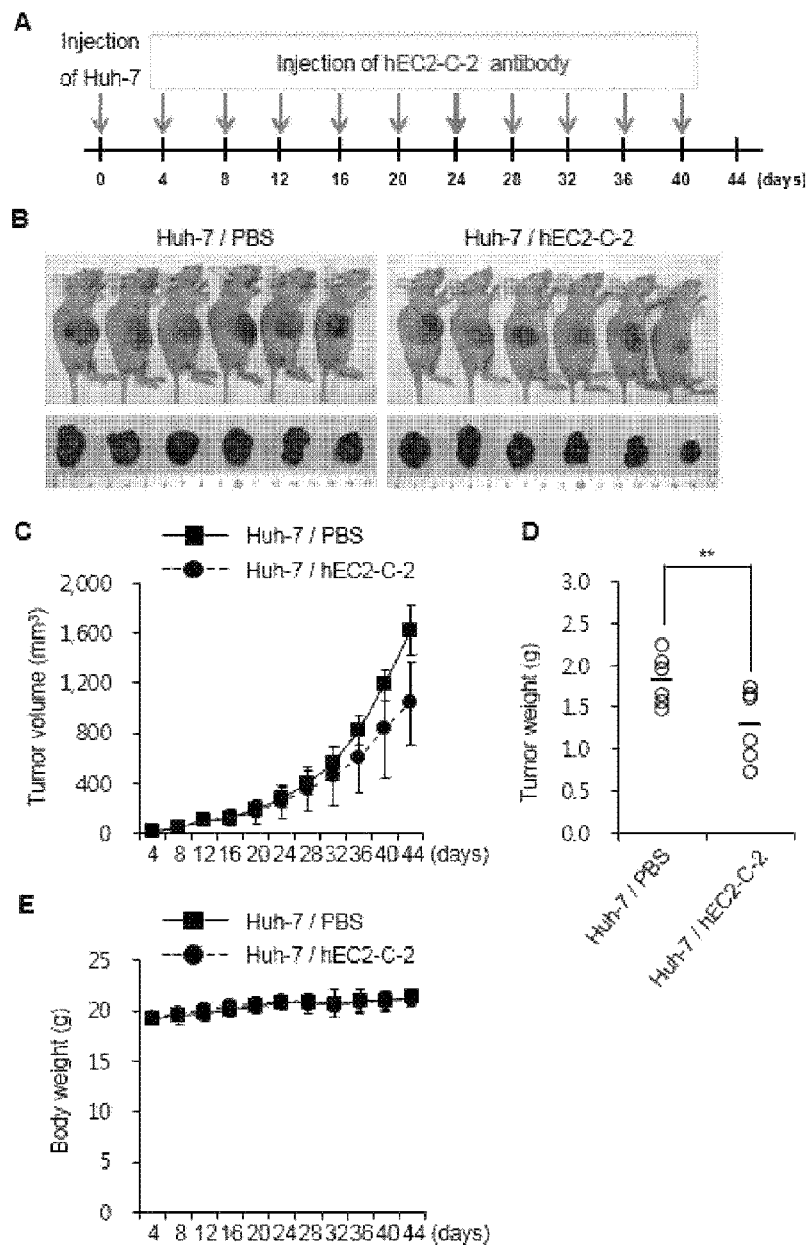

【Figure 15】
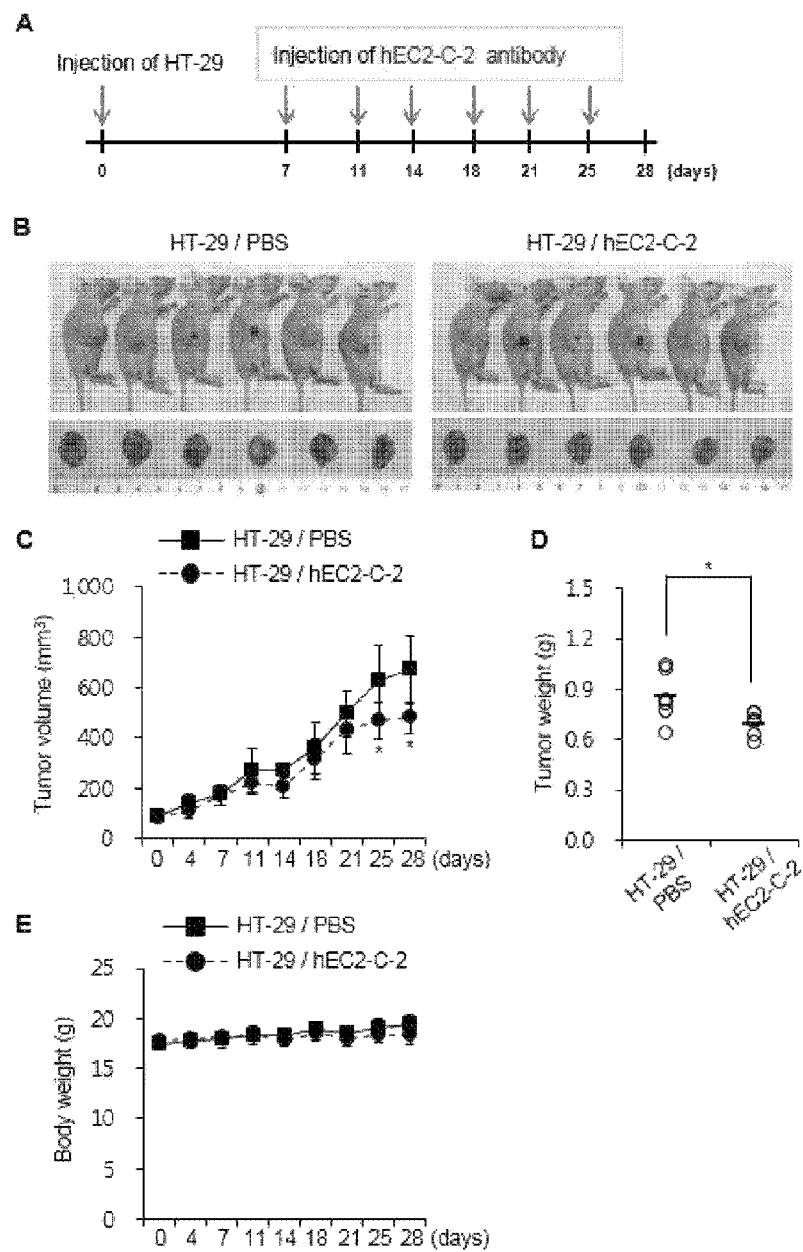

【Figure 16】
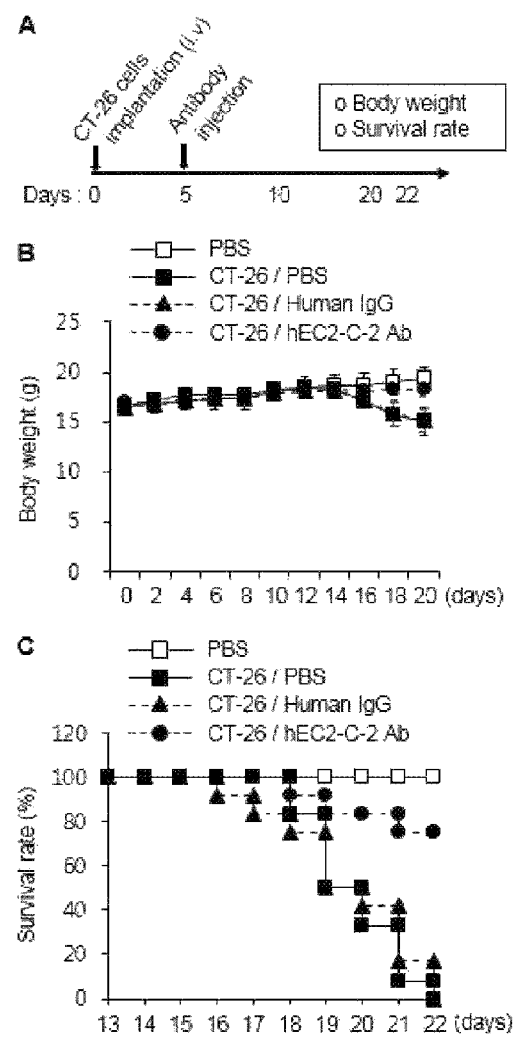

【Figure 17】
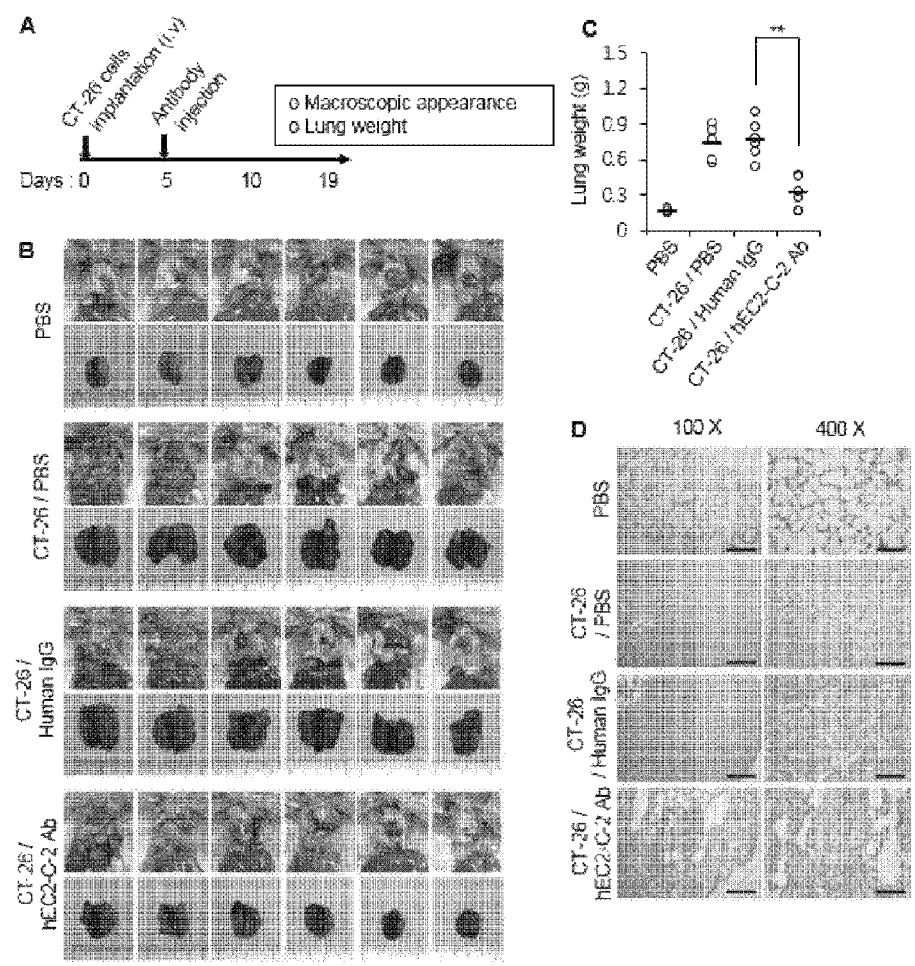

SEQUENCE LISTING

<160> NUMBER OF SEQ ID NOS: 25

<210> SEQ ID NO 1
<211> LENGTH: 27
<212> TYPE: PRT
<213> ORGANISM: Homo sapiens

<400> SEQUENCE: 1

Thr Ala Cys Ala Tyr Leu Leu Asn Arg Thr Leu Trp Asp Arg Cys Glu
1               5                   10                  15

Ala Pro Pro Arg Val Val Pro Trp Asn Cys Thr
            20                  25

<210> SEQ ID NO 2
<211> LENGTH: 27
<212> TYPE: PRT
<213> ORGANISM: mouse

<400> SEQUENCE: 2

Thr Glu Cys Ala Tyr Leu Arg Asn Asp Thr Leu Trp Asn Leu Cys Glu
1               5                   10                  15

Ala Pro Pro His Val Val Pro Trp Asn Cys Thr
            20                  25

<210> SEQ ID NO 3
<211> LENGTH: 10
<212> TYPE: PRT
<213> ORGANISM: mouse

<400> SEQUENCE: 3

Gly Phe Ser Leu Thr Ser Tyr Gly Val Thr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: humanized

<400> SEQUENCE: 4

Gly Phe Ser Leu Thr Ser Tyr Gly Val Thr
1               5                   10

<210> SEQ ID NO 5
<211> LENGTH: 16
<212> TYPE: PRT
<213> ORGANISM: mouse

<400> SEQUENCE: 5

Val Ile Trp Ser Asp Gly Ser Thr Asn Tyr Gln Ser Ala Leu Ile Ser
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: humanized

<400> SEQUENCE: 6

Val Ile Trp Ser Asp Gly Ser Thr Asn Tyr Gln Ser Ala Leu Ile Ser
1               5                   10                  15

<210> SEQ ID NO 7
<211> LENGTH: 9
<212> TYPE: PRT
<213> ORGANISM: mouse

<400> SEQUENCE: 7

Pro Ser Asn Tyr Tyr Tyr Phe Asp Tyr
1               5

<210> SEQ ID NO 8
<211> LENGTH: 9
<212> TYPE: PRT
<213> ORGANISM: Artificial Sequence
<220> FEATURE:
<223> OTHER INFORMATION: humanized

<400> SEQUENCE: 8

Pro Ser Asn Tyr Tyr Tyr Phe Asp Tyr
1               5

<210> SEQ ID NO 9
<211> LENGTH: 17
<212> TYPE: PRT
<213> ORGANISM: mouse

<400> SEQUENCE: 9

Lys Ser Ser Gln Ser Leu Phe Asp Arg Arg Thr Arg Lys Thr Tyr Leu
1               5                   10                  15
Ala

<210> SEQ ID NO 10
<211> LENGTH: 17
<212> TYPE: PRT
<213> ORGANISM: Artificial Sequence
<220> FEATURE:
<223> OTHER INFORMATION: humanized

<400> SEQUENCE: 10

Lys Ser Ser Gln Ser Leu Phe Asp Arg Arg Thr Arg Lys Thr Tyr Leu
1               5                   10                  15
Ala

<210> SEQ ID NO 11
<211> LENGTH: 7
<212> TYPE: PRT
<213> ORGANISM: mouse

<400> SEQUENCE: 11

Trp Ala Ser Thr Arg Glu Ser
1               5

<210> SEQ ID NO 12
<211> LENGTH: 7
<212> TYPE: PRT
<213> ORGANISM: Artificial Sequence
<220> FEATURE:
<223> OTHER INFORMATION: humanized

<400> SEQUENCE: 12

Trp Ala Ser Thr Arg Glu Ser
1               5

<210> SEQ ID NO 13
<211> LENGTH: 8
<212> TYPE: PRT
<213> ORGANISM: mouse

<400> SEQUENCE: 13

Lys Gln Ser Tyr Asn Leu Phe Thr
1               5

<210> SEQ ID NO 14
<211> LENGTH: 8
<212> TYPE: PRT
<213> ORGANISM: Artificial Sequence
<220> FEATURE:
<223> OTHER INFORMATION: humanized

<400> SEQUENCE: 14

Lys Gln Ser Tyr Asn Leu Phe Thr
1               5

<210> SEQ ID NO 15
<211> LENGTH: 133
<212> TYPE: PRT
<213> ORGANISM: mouse

<400> SEQUENCE: 15

Gln Val Gln Leu Glu Glu Ser Gly Pro Gly Leu Val Ala Pro Ser Gln
1               5                   10                  15

Ser Leu Ser Ile Ile Cys Thr Val Ser Gly Phe Ser Leu Thr Ser Tyr
            20                  25                  30

Gly Val Thr Trp Val Arg Gln Pro Pro Gly Lys Gly Leu Glu Trp Leu
        35                  40                  45

Gly Val Ile Trp Ser Asp Gly Ser Thr Asn Tyr Gln Ser Ala Leu Ile
    50                  55                  60

Ser Arg Leu Thr Ile Ser Arg Asp Asn Ser Lys Ser Gln Ala Phe Leu
65                  70                  75                  80

Lys Leu Asn Ser Leu Gln Thr Asp Asp Thr Ala Thr Tyr Tyr Cys Ala
                85                  90                  95

Arg Pro Ser Asn Tyr Tyr Tyr Phe Asp Tyr Trp Gly Gln Gly Thr Thr
            100                 105                 110

Leu Thr Val Ser Ser Ala Thr Thr Thr Ala Pro Ser Val Tyr Pro Leu
        115                 120                 125

Val Pro Arg Ser Ser
    130

<210> SEQ ID NO 16
<211> LENGTH: 117
<212> TYPE: PRT
<213> ORGANISM: Artificial Sequence
<220> FEATURE:
<223> OTHER INFORMATION: humanized

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ser Tyr
            20                  25                  30

Gly Val Thr Trp Val Arg Gln Ala Pro Gly Lys Gly Leu Glu Trp Leu
        35                  40                  45

Gly Val Ile Trp Ser Asp Gly Ser Thr Asn Tyr Gln Ser Ala Leu Ile
    50                  55                  60

Ser Arg Leu Thr Ile Ser Arg Asp Asn Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg Pro Ser Asn Tyr Tyr Tyr Phe Asp Tyr Trp Gly Gln Gly Thr Leu
            100                 105                 110

Val Thr Val Ser Ser
        115

<210> SEQ ID NO 17
<211> LENGTH: 124
<212> TYPE: PRT
<213> ORGANISM: mouse

<400> SEQUENCE: 17

Asp Ile Val Met Thr Gln Ser Pro Ser Ser Leu Ala Val Ser Ala Gly
1               5                   10                  15

Glu Arg Val Thr Leu Ser Cys Lys Ser Ser Gln Ser Leu Phe Asp Arg
            20                  25                  30

Arg Thr Arg Lys Thr Tyr Leu Ala Trp Tyr Gln Gln Lys Pro Gly Gln
            35                  40                  45

Ser Pro Lys Leu Leu Ile Ser Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Phe Thr Phe Gly Gly Gly Thr Lys Leu Glu Ile Lys
                100                 105                 110

Arg Ala Asp Ala Ala Pro Thr Val Ser Ala Cys Thr
            115                 120

<210> SEQ ID NO 18
<211> LENGTH: 112
<212> TYPE: PRT
<213> ORGANISM: Artificial Sequence
<220> FEATURE:
<223> OTHER INFORMATION: humanized

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asp Arg
            20                  25                  30

Arg Thr Arg Lys Thr Tyr Leu Ala Trp Tyr Gln Gln Lys Pro Gly Lys
            35                  40                  45

Ala Pro Lys Leu Leu Ile Ser Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Lys Gln
                85                  90                  95

Ser Tyr Asn Leu Phe Thr Phe Gly Gln Gly Thr Lys Val Glu Ile Lys
                100                 105                 110

<210> SEQ ID NO 19
<211> LENGTH: 399
<212> TYPE: DNA
<213> ORGANISM: mouse

<400> SEQUENCE: 19
caggttcagc tggaggagtc aggacctggc ctggtggcgc cctcacagag cctgtccatc      60
atatgcactg tctcaggatt ctccttaacc agctatggtg taacctgggt tcgccagcct     120
ccaggaaagg gtctggagtg gctgggagta atatggagtg acgggagcac aaattatcag     180
tcagctctca tatccagact gaccatcagc agggataact ccaagagcca agctttctta     240
aaactgaaca gtctgcaaac tgatgacaca gccacgtact actgtgccag acctagtaac     300
tactactact ttgactactg gggccaaggc accactctca cagtctcctc agctacaaca     360
acagccccat ctgtctatcc cttggtccct agatcttcc                            399

<210> SEQ ID NO 20
<211> LENGTH: 351
<212> TYPE: DNA
<213> ORGANISM: Artificial Sequence
<220> FEATURE:
<223> OTHER INFORMATION: humanized

<400> SEQUENCE: 20

```
gaggtgcagc tggtggagtc tggcggtggc ctggtgcagc caggggggctc actccgtttg    60
tcctgtgcag cttctggctt ctccttaacc agctatggtg taacctgggt gcgtcaggcc   120
ccgggtaagg gcctggaatg gctgggagta atatggagtg acgggagcac aaattatcag   180
tcagctctca tatccagact gactataagc aggacaact ccaaaaacac agcctacctg   240
cagatgaaca gcctgcgtgc tgaggacact gccgtctatt attgtgccag acctagtaac   300
tactactact ttgactactg gggtcaagga accctggtca ccgtctcctc g            351
```

<210> SEQ ID NO 21
<211> LENGTH: 372
<212> TYPE: DNA
<213> ORGANISM: mouse

<400> SEQUENCE: 21

```
gatattgtga tgacacagtc tccatcctcc ctggctgtgt cagcaggaga gagggtcact    60
ttgagctgca aatccagtca gagtctgttc gacagaagaa cccgaaagac ctacttggct   120
tggtaccagc agaaaccagg gcagtctcct aaactgctga tctcctgggc atccactagg   180
gaatctgggg tccctgatcg cttcacaggc agtggatctg ggacagattt cactctcacc   240
atcagcagtg tgcaggctga agacctggca gtttattatt gcaaacaatc ttataatctg   300
ttcacgttcg ggggggggac caagctggaa ataaaacggg ctgatgctgc accaactgta   360
tccgcatgca cc                                                        372
```

<210> SEQ ID NO 22
<211> LENGTH: 336
<212> TYPE: DNA
<213> ORGANISM: Artificial Sequence
<220> FEATURE:
<223> OTHER INFORMATION: humanized

<400> SEQUENCE: 22

```
gatatccaga tgacccagtc cccgagctcc ctgtccgcct ctgtgggcga tagggtcacc    60
atcacctgca atccagtca gagtctgttc gacagaagaa cccgaaagac ctacttggct   120
tggtatcaac agaaaccagg aaaagctccg aagctactga tttcctgggc atccactagg   180
gaatctggag tcccttctcg tttctctgga tcgggatctg ggacggattt cactctgacc   240
atcagcagtc tgcagccgga agacttcgca acttattact gtaaacaatc ttataatctg   300
ttcacgttcg gacagggtac caaggtggag atcaaa                              336
```

<210> SEQ ID NO 23
<211> LENGTH: 20
<212> TYPE: DNA
<213> ORGANISM: Artificial Sequence
<220> FEATURE:
<223> OTHER INFORMATION: CpG oligonucleotide

<400> SEQUENCE: 23

```
agcagcgttc gtgtcggcct                                                 20
```

<210> SEQ ID NO 24
<211> LENGTH: 27
<212> TYPE: DNA
<213> ORGANISM: Artificial Sequence
<220> FEATURE:
<223> OTHER INFORMATION: primer

```
<400> SEQUENCE: 24
ctcgagatgt gtacgggaaa atgtgcc                                    27

<210> SEQ ID NO 25
<211> LENGTH: 29
<212> TYPE: DNA
<213> ORGANISM: Artificial Sequence
<220> FEATURE:
<223> OTHER INFORMATION: primer

<400> SEQUENCE: 25
aagcttttgt gaggtgtgtc ctgtttttt                                  29
```

VACCINE COMPOSITION COMPRISING CYCLIC PEPTIDES, ANTIBODIES TO THE CYCLIC PEPTIDES OR AN ANTICANCER COMPOSITION COMPRISING THE SAME

TECHNICAL FIELD

The present invention relates to a vaccine composition comprising cyclic peptides, antibodies to the cyclic peptides, or an anticancer composition comprising the same.

BACKGROUND ART

An expression of mRNA of transmembrane 4 superfamily member 5 protein (TM4SF5) in human cancer has been observed in pancreatic cancer, soft tissue sarcoma, gastric cancer, carcinoma of the papilla vateri, and colorectal cancer. TM4SF5 plays an important role in the formation of hepatocellular carcinoma (HCC) through the induced morphological elongation and epithelial-mesenchymal transition, and causes an abnormal cell growth in vitro and a tumor formation in vivo. It has been reported that TM4SF5 expression-induced uncontrolled cell proliferation and neovascularization occur when inhibiting integrin α2 function in a collagen type I environment due to extracellular interactions between TM4SF5 and integrin α2. 4'-(p-toluenesulfonyl-amido)-4-hydroxychalcone) (TSAHC), a synthetic inhibitor targeting TM4SF5, inhibited HCC growth and metastasis in vitro and in vivo. These facts show that the role of TM4SF5 in HCC formation is a novel molecular target for the development of HCC therapeutic drugs.

HCC is one of the most common cancers in the world and has been particularly prevalent in in Asia and the sub-Saharan Africa. It has been known that most of the developments of HCCs are a multistep process involving dysplastic nodule, early HCC, highly well differentiated HCC, and intermediate and low differentiated HCC.

Colon cancer is the third most common cancer in the world, and it is more common in developed countries than in developing countries. The most frequent mutation genes in colorectal cancer are APC, β-catenin, AXIN1, AXIN2, TCF7L2 or NKD1, which are associated with the Wnt-APC-β-catenin signaling pathway.

Meanwhile, cellular immunity, especially cytotoxic T cells (called as CTLs) plays an important role in the exclusion of tumor cells, virus-infected cells, and the like, by the living body. In the case of the exclusion of tumor cells, CTL recognizes a complex of antigenic peptides (tumor antigen peptides) and Major Histocompatibility Complex (MHC) class I antigen (called as HLA class I antigens in case of human) on the tumor cells, and attack and destroy the tumor cell. That is, the tumor antigen peptide is produced by synthesizing a tumor-specific protein, i.e., a tumor antigen protein, and then intracellularly degrading it by a protease in a cell. The resulting tumor antigen peptide binds to the MHC class I antigen (HLA class I antigen) in the endoplasmic reticulum to form a complex, which is transferred to the cell surface and presented as an antigen. The antitumor effects are exhibited through recognizing the antigen-presenting complex by the tumor-specific CTL and producing scytotoxic action and lymphokines. According to the resolution of such a series of actions, a therapy is developing in which a tumor antigen protein or tumor antigen peptide is used as a cancer immunotherapeutic agent (cancer vaccine) to enhance cancer-specific CTLs in bodies of cancer patients.

Numerous papers and patent documents are referenced and their citations are represented throughout this specification. The disclosures of the cited papers and patent documents are incorporated herein by reference in their entirety to more clearly illustrate the state of the art to which the present invention pertains and the contents of the present invention.

PRIOR PATENT DOCUMENT

Korean Laid-open Patent Publication No. 10-2015-0122159

DISCLOSURE

Technical Problem

The present inventors have made efforts to develop vaccines and antibodies that can diagnose, prevent and treat cancer. As a result, we prepared novel antibodies and antigen-binding fragments thereof, which bind to peptides of tumor-specific antigen, TM4SF5 with high affinity, and confirmed excellent inhibitory activity of the antibodies against the growth, metastasis and invasion of cancer cells, and then has been completed the present invention.

Therefore, an object of the present invention is to provide a cyclic peptide vaccine composition.

Other object of the present invention is to provide antibodies to the cyclic peptides or antigen-binding fragments thereof.

Another object of the present invention is to provide a nucleic acid molecule encoding a heavy chain variable region of said antibodies or antigen-binding fragment thereof.

Another object of the present invention is to provide a nucleic acid molecule encoding a light chain variable region of the above antibodies or antigen-binding fragment thereof.

Another object of the present invention is to provide a pharmaceutical composition for preventing or treating cancer.

Still other object of the present invention is to provide a kit for diagnosing cancer.

Other objects and advantages of the present invention will become more apparent from the following detailed description of the invention, claims and drawings.

Means for Resolving the Problem

In order to achieve the above objects, the present invention provides a vaccine composition comprising peptides consisting of an amino acid sequence selected from the group consisting of SEQ ID NOS: 1 to 2; or peptides consisting amino acid sequence selected from the group consisting of cyclic peptides linked by a disulfide bond between the $3^{rd}$ cystein amino acid and the 26th cystein amino acid in sequences of SEQ ID NO: 1 to SEQ ID NO: 2, as an effective ingredient.

In one embodiment of the present invention, the peptide vaccine composition is preferably one which encapsulated in liposome with immunostimulatory oligonucleotides, but is not limited thereto.

Term "liposome" as used herein means a lipid carrier to be prepared by forming a lipid bilayer. Generally, liposomes are biocompatible and have amphipathic property, and thus can pass through hydrophobic membranes under the situation including hydrophilic materials therein. The diameter of the liposome is generally 20-2,000 nm, but is not limited thereto, and may vary in size depending on the method of preparation and the length of the nucleotide to be delivered.

According to a preferred embodiment of the present invention, the liposome of the present invention is a mixture of CHEMS and DOPE. The molar ratio of DOPE:CHEMS in the liposome used in the present invention is preferably 7:3-3:7, more preferably 4.5:5.5-5.5:4.5, and most preferably 5.0:5.0.

The liposomes of the present invention can be prepared by various methods known in the art, and preferably utilize an organic solvent-mixing method or an interfacial agent-mixing method (U.S. Pat. No. 5,705,385; U.S. patent application Ser. No. 08/660,025). More preferably, the liposome is prepared by the process comprising mixing DOPE and CHEMS, evaporating it with nitrogen gas to make a solvent free lipid film, and then dissolving it in an alcohol solution, and finally mixing it with a water-soluble nucleotide mixture.

When the preparation of the liposome of the present invention is carried out through the mixing of organic solvent, the organic solvent used therein includes chloroform, methanol, ethanol, n-propanol or butanol. Preferably, the organic solvent is ethanol.

The term "encapsulating", as used herein, means enclosing the material to be transported into a relatively stable shell for efficient in vivo transportation.

As used herein, the term "immunostimulatory" means to induce an initial immune response or to increase the existing immune response to an antigen to the measurable extent.

Immunostimulatory oligonucleotides that may be used in the present invention include any immunostimulatory oligonucleotides known in the art. For example, the immunostimulatory oligonucleotides may be palindrome to form a hairpin secondary structure, CpG motifs, CpT motifs or oligonucleotides comprising multiple G domains or other known immunostimulatory sequence (ISS). For example, the immunostimulatory oligonucleotides used in the present invention include immunostimulatory oligonucleotides as disclosed in the Laid-open U.S. Patent Application No. 20080045473, WO 2006/063152 or WO 1998/18810. Specific examples of the immunostimulatory oligonucleotides containing the CpG motif include the CpG oligonucleotides developed by the present inventors as disclosed in WO 2006/0027-080596.

Immunostimulatory oligonucleotides used as effective ingredients in the present invention include natural-occurring nucleotides, backbone-modified nucleotides (e.g., peptide nucleic acids (PNA) (M. Egholm, et al., Nature, 365: 566-568 (1993)), phosphorothioate DNA, phosphorodithioate DNA, phosphoroamidate DNA, amide-linked DNA, MMI-linked DNA, 2'-O-methyl RNA, alpha-DNA and methylphosphonate DNA, sugar-modified nucleotide (e.g., 2'-O-methyl RNA, 2'-fluoro RNA, 2'-amino RNA, 2'-O-alkyl DNA, 2'-O-allyl DNA, 2'-O-alkinyl DNA, hexose DNA, pyranosyl RNA and anhydrohexitol DNA), and base-modified nucleotides (e.g., C-5 substituted pyrimidine (wherein the substituent includes fluoro-, bromo-, chloro-, iodo-, methyl-, ethyl-, vinyl-, formyl-, ethytyl-, propynyl-, alkynyl-, thiazolyl-, imidazolyl- and pyridyl-), 7-deazapurines with C-7 substituents (the substituents include fluoro-, bromo-, chloro-, iodo-, methyl-, ethyl-, vinyl-, formyl-, alkynyl-, alkenyl-, thiazolyl-, imidazolyl- and pyridyl-), inosine and diaminopurine). Preferably, the oligonucleotide of the present invention is natural nucleotide.

According to a preferred embodiment of the present invention, the immunostimulatory oligonucleotides of the present invention have a phospho-diester backbone or a phosphorothioate backbone.

The immunostimulatory oligonucleotides used in the present invention is not particularly limited in the length, and is preferably 8-100 nucleotides in length, more preferably 15-50 nucleotides in length, and most preferably about 13-25 nucleotides in length. Preferably, the immunostimulatory oligonucleotide of the present invention is an oligonucleotide of SEQ ID NO: 23 sequence.

As used herein, the term "epitope" refers to the site of an antigen that interacts with antibodies. More specifically, an epitope refers to a protein determinant capable of specifically binding to an immunoglobulin or T-cell receptor. In addition, the epitope of the present invention includes any molecule or substance capable of increasing the immune response. For example, epitopes of the invention include, but are not limited to, peptides, nucleic acids encoding these peptides, and glycoproteins.

As used in herein, the term "peptides (peptide)" mean a linear molecule formed by peptide binding between amino acid residues, and the term "peptide epitopes", as used in herein mean peptides comprising epitopes capable of inducing specific responses of B cells and/or T cells.

The composition of the present invention may include other drugs or other immunoadjuvants to provide additional immunostimulatory effects. The kinds of the immunoadjuvants are well known in the art (Vaccine Design—The Subunit and Adjuvant Approach, 1995, Pharmaceutical Biotechnology, Volume 6, Eds. Powell, M. F., and Newman, M. J., Plenum Press, New York and London, ISBN 0-306-44867-X). Preferably, the immunoadjuvant included in the composition of the present invention comprises an aluminum salt or a calcium salt (e.g., hydroxide or phosphate).

Specific examples of preferred immunoadjuvants include, but are not limited to, the following: aluminum salts or calcium salts (hydroxides or phosphates), oil-in-water emulsions (WO 95/17210, EP 0 399 843) or fine particular carriers such as liposomes (WO 96/33739), saponin fraction (e.g., Quil A) having immunological adjuvant activity derived from the South American tree *Quillaja Saponaria Molina*, 3 De-O-cylated monophosphoryl lipid A, muramyl dipeptide, 3-O-decylated monophosphoryl lipid A (3DMPL).

The vaccine composition of the present invention can be applied to the treatment of various conditions or diseases and examples of such conditions or diseases include colon cancer, liver cancer, stomach cancer, lung cancer, breast cancer, ovarian cancer, liver cancer, bronchial cancer, nasopharyngeal cancer, laryngeal cancer, pancreatic cancer, bladder cancer, colorectal cancer, cervical cancer, brain cancer, prostate cancer, bone cancer, skin cancer, thyroid cancer, pituitary cancer and ureter cancer.

The pharmaceutically acceptable carriers to be included in the pharmaceutical composition of the present invention are those conventionally used in the preparation and include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, etc., but are not limited thereto. The pharmaceutical composition of the present invention may further include a lubricant, a wetting agent, a sweetener, a flavoring agent, an emulsifying agent, a suspending agent, a preservative, etc., in addition to the above components. Suitable pharmaceutically acceptable carriers and formulations are described in detail in Remington's Pharmaceutical Sciences (19th ed., 1995).

The pharmaceutical composition of the present invention can be administered orally or parenterally, preferably parenterally. In the case of parenteral administration, the composition can be administered by intravenous injection, subcutaneous injection, muscle injection, intraperitoneal injection, percutaneous administration, etc.

The appropriate dosage of the pharmaceutical composition of the present invention may vary depending on factors such as the formulation method, the administration mode, the age, body weight, sex of the patient, pathological condition, food, administration time, administration route, excretion rate and responsiveness. On the other hand, the oral dosage amount of the pharmaceutical composition of the present invention is preferably 0.001-10,000 mg/kg (body weight) per day.

The pharmaceutical composition of the present invention may be formulated into a unit dosage form by using a pharmaceutically acceptable carrier and/or excipient according to a method which can be easily carried out by those having ordinary skill in the art to which the present invention belongs, or by incorporating it into a multi-dose container. In this case, the formulations may be in the form of solutions, suspensions or emulsions in oils or aqueous media, or in the form of extracts, powders, granules, tablets or capsules, and may additionally contain dispersing or stabilizing agents The invention also provides antibodies to peptides comprising amino acid sequences selected from the group consisting of SEQ ID NOS: 1 to 2; or peptides comprising amino acid sequence selected from the group consisting of cyclic peptides linked by a disulfide bond between the 3' cystein amino acid and the $26^{th}$ cystein amino acid in sequences of SEQ ID NOs: 1 to 2, or antigen-binding fragments thereof.

In one embodiment of the present invention, the antibodies preferably comprise a heavy chain variable region having a heavy chain complementarity determining region (CDR) amino acid sequence of CDRH1 consisting of the sequence of SEQ ID NO: 3 or SEQ ID NO: 4 of the sequence listing, CDRH2 consisting of the sequence of SEQ ID NO: 5 or SEQ ID NO: 6 of the sequence listing, and CDRH3 consisting of the sequence of SEQ ID NO: 7 or SEQ ID NO: 8 of the sequence listing; and the light chain variable region having a light chain CDR amino acid sequence of CDRL1 consisting of the sequence of SEQ ID NO: 9 or 10 of the sequence listing, CDRL2 consisting SEQ ID No. 11 or 12 of the sequence listing and CDRL3 consisting of SEQ ID No. 13 or 14, but are not limited thereto.

The inventors of the present invention designed cyclic peptides corresponding to extracellular domain 2 (EC2) of TM4SF5, encapsulated cyclic hTM4SF5 peptides and MB-ODN 4531 (O) in phosphatidyl-β-oleoyl-γ-palmitoyl ethanolamine (DOPE): cholesterol hemisuccinate (CHEMS) complex to produce cyclic peptide-specific antibodies. in mice after immunization. Mice, as a metastatic model, were administered with intravenous injection of a mouse colorectal cancer cell line CT-26 to induce tumors in the lung. The mice immunized with peptides vaccine exhibited the increase of survival, and the decrease in the number of metastatic lung nodules and the growth of lung tumors, suggesting the anti-metastatic effect of the peptides vaccine. The present inventors used the cyclic peptides-like structural motif of TM4SF5 as an antigen and successfully isolated monoclonal antibodies recognizing the TM4SF5 protein having a low off-rate. The inventors also prepared humanized antibodies and evaluated their reactivity in vitro and in vivo. Importantly, the inventors have found inhibitory effects of the humanized anti-TM4SF5 antibodies of the invention on the formation and growth of liver and colon cancers. The humanized anti-TM4SF5 antibodies injected intravenously also inhibited lung metastasis established by intravenous injection of colon cancer cells into a mouse metastasis model.

Therefore, the main content of the present invention relates to the following:

i) TM4SF5 is expressed in liver cancer, colorectal cancer, etc., and affects the growth of cancer.

ii) A production of antibody to the cyclic peptide by synthesizing cyclic peptides corresponding to extracellular domain 2 (EC2) of TM4SF5, preparing cyclic peptide-CpG-DNA-liposome complex, and then immunizing mice with it.

iii) Verification of vaccine efficacy for a metastasis of colon cancer (using CT-26 cells) of cyclic peptide-CpG-DNA-liposome complex used as a vaccine.

iv) Production of monoclonal antibodies by fusing splenocytes from mice immunized with cyclic peptide-CpG-DNA-liposome complexes.

v) Production of humanized anti-TM4SF5 antibodies based on mouse anti-TM4SF5 monoclonal antibodies.

vi) Evaluation of humanized anti-TM4SF5 antibodies on the inhibitory effect against hepatocarcinoma and colon cancer, and against metastasis of the colon cancer.

Hereinafter, the present invention will be described in detail.

Anti-TM4SF5 Humanized Antibodies and their Antigen Binding Fragments

The antibodies of the present invention have a specific binding ability to TM4SF5.

The term "antibodies", as used herein when referring to TM4SF5 is a specific antibody to TM4SF5, which specifically binds to a specific epitope of TM4SF5 and includes not only complete forms of the antibodies but also antigen-binding fragments (antibody fragments) of antibody molecule.

The term "humanized" refers to the case where antibodies are wholly or partly of non-human origin, for example, murine antibodies obtained by immunizing mice with the antigen of interest, or in the case of the chimeric antibodies based on such murine antibodies, refers to the fact that the immune response in humans can be avoided or minimized by replacing specific amino acids in the framework region of the heavy chain and light chain and in the constant domain. All antibodies are known to have the potential to induce a human anti-antibody response that is somewhat related to the degree of "humanness" of the antibodies being discussed. Non-human antibodies tend to be more immunogenic than human antibodies, although immunogenicity and thereby precise prediction of the human anti-antibody response of certain antibodies is not possible. Chimeric antibodies in which exogenous (usually rodent) constant regions have been replaced by sequences of human origin have generally been shown to be less immunogenic than antibodies of complete exogenous origin, and trends in therapeutic antibodies are directed toward humanized or fully human antibodies. In the case of chimeric antibodies or other antibodies of non-human origin, it is desirable to consequently reduce the risk of human anti-antibodies response by humanizing them.

Many methods of humanizing antibody sequences are known in the art; See, for example, reviewed by Almagro & Fransson (2008) Front Biosci. 13: 1619-1633. One commonly used method is CDR grafting comprising identifying human germline gene counterparts to murine variable region genes and grafting murine CDR sequences into such frameworks, e.g., in the case of murine-derived chimeric antibodies. CDR grafting may be based on the Kabat CDR definition, but a more recent publication (Magdelaine-Beuzelin et al. (2007) Crit Rev. Oncol Hematol. 64: 210-225) suggests the IMGT® definition (the international ImMunoGeneTics information system®, www.imgt.org) could improve the outcome of humanization (see Lefranc et al. (2003), IMGT unique numbering for immunoglobulin and T cell receptor variable domains and Ig superfamily V-like domains, Dev. Comp Immunol. 27, 55-77). As CDR grafting can reduce the binding specificity and affinity of CDR grafted non-human antibodies, and thus can reduce the biological activity, the binding specificity and affinity of the parent antibodies can be re-established by typically introducing a return mutation (sometimes, referring to "framework restoration") into the selected position of the CDR grafted antibodies in the framework region. Identification of sites for possible reverse mutations can be performed using information available in the literature and antibodies database. The amino acid residues that are candidates for the return mutation are typically those located on the surface of the antibody molecules, while residues that have a hidden or low degree of surface exposure will generally not be altered. An alternative humanization technique for CDR grafting and reverse mutation is resurfacing which alters surface residues to human residues, while maintaining the surface-unexposed residues of non-human origin.

In certain instances, it may also be desirable to alter one or more CDR amino acid residues to enhance binding affinity for the target epitope. This is known as "affinity maturation", and can be performed in combination with the humanization, under the conditions that humanization of antibodies results in decreased binding specificity or affinity and the binding specificity or affinity cannot be sufficiently improved by the return mutation alone. Various affinity maturation methods, for example, in vitro scanning saturation mutagenesis method disclosed in Burks et al. (1997) PNAS USA, vol. 94, pp. 412-417) and the stepwise in vitro affinity maturation method of Wu et al. (1998) PNAS USA, vol. 95, pp. 6037-6042 are known in the art.

The complete antibody is a structure with two full-length light chains and two full-length heavy chains, each light chain is linked by a disulfide bond with a heavy chain. The heavy chain constant region has gamma (γ), mu (μ), alpha (α), delta (δ) and epsilon (ε) types and has gamma 1 (γ 1), gamma 2(γ 2), gamma 3 (γ 3), gamma 4 (γ 4), alpha 1 (γ 1) and alpha 2 (γ 2) as a subclass. The constant region of the light chain has kappa (κ) and lambda (λ) types.

An antigen-binding fragment of an antibody molecule or an antibody fragment refers to a fragment having an antigen-binding function and includes Fab, F (ab'), F (ab')$_2$, Fv, and the like. Among the antibodies fragments, Fab has one antigen-binding site in a structure having a variable region of a light chain and a heavy chain, a constant region of a light chain, and the first constant region ($C_{H1}$) of a heavy chain. Fab' differs from Fab in that it has a hinge region that contains at least one cysteine residue at the C-terminus of the heavy chain $C_{H1}$ domain. F(ab')$_2$ antibodies are produced by disulfide linkage of the cysteine residues in the hinge region of the Fab'. Fv is a minimal antibody piece having only a heavy chain variable region and a light chain variable region, and recombinant techniques for producing Fv fragments are disclosed in PCT International Publication Nos. WO 88/10649, WO 88/106630, WO 88/07085, WO 88/07086, and WO 88/09344. In the double-chain Fv, the heavy chain variable region and the light chain variable region are linked by a non-covalent bond, and in the single-chain Fv, since the variable region of the heavy chain and the variable region of the light chain are linked by convalent bond via the peptides linker or directly linked at the C-terminus, a dimer-like structure such as double-chain Fv can be made. These antibody fragments can be obtained using protein hydrolytic enzymes (for example, Fab can be obtained by restrictly cleaving the whole antibody with papain, F(ab')$_2$ fragments can be obtained by cleaving it with pepsin), and also can be constructed by gene recombinant technology.

According to one embodiment of the present invention, the antibody in the present invention is either Fab-type or complete antibody type. In addition, the heavy chain constant region can be selected from any one isotype of gamma (γ), mu (μ), alpha (α), delta (δ), or epsilon (ε). In one particular example, the constant region is gamma 1 (IgG1), gamma 2 (IgG2), gamma 3 (IgG3) or gamma 4 (IgG4), and in other specific examples, the constant region is IgG2a isotype. The light chain constant region may be kappa or lambda type. In one specific example, the light chain constant region is kappa type.

As used herein, the term "heavy chain" means all of a variable region domain $V_H$ comprising an amino acid sequence with sufficient variable region sequence to confer specificity to an antigen and a full length heavy chain comprising three constant region domains $C_{H1}$, $C_{H2}$ and $C_{H3}$ and fragments thereof. In addition, the term "light chain" as used herein means a full-length light chain comprising the variable region domain $V_L$ and the constant region domain $C_L$ comprising an amino acid sequence having a sufficient variable region sequence to confer specificity to the antigen, and fragments thereof.

As used herein, the term "complementarity determining region (CDR)" means the amino acid sequence of the immunoglobulin heavy chain and the hypervariable region of the light chain (Kabat et al. *Sequences of Proteins of Immunological Interest*, 4th Ed., U.S. Department of Health and Human Services, National Institutes of Health (1987)). The heavy chains (CDRH1, CDRH2 and CDRH3) and light chains (CDRL1, CDRL2 and CDRL3) contain three CDRs, respectively. CDR provides the key contact residues for the binding of antibodies to an antigen or epitope.

The antibody or the antibody fragments of the present invention may comprise variants of the amino acid sequences described in the attached Sequence Listing in the range that TM4SF5 can be specifically recognized. For example, additional changes can be made to the amino acid sequence of antibody to further improve the binding affinity and/or other biological properties of the antibody. Such modifications include, for example, deletion, insertion and/or substitution of amino acid sequence residues of antibody. Such amino acid variations are made based on the relative similarity of amino acid side chain substituents, e.g., hydrophobicity, hydrophilicity, charge, size, and the like. By analysis of the size, shape and type of amino acid side chain substituents, it can be seen that all of arginine, lysine and histidine are positively charged residues; and alanine, glycine and serine have similar sizes; and phenylalanine, tryptophan and tyrosine have similar shapes. Thus, based on these considerations, arginine, lysine and histidine; alanine, glycine and serine; and phenylalanine, tryptophan and tyrosine can be considered as being biologically functional equivalents.

In introducing mutations, the hydropathic index of amino acids can be considered. Each amino acid is given a hydrophobic index according to its hydrophobicity and charge: Isoleucin (+4.5); Valine (+4.2); Leucine (+3.8); Phenylalanine (+2.8); Cysteine/cystaine (+2.5); Methionine (+1.9);

Alanine (+1.8); Glycine (−0.4); Threonine (−0.7); Serine (−0.8); Tryptophan (−0.9); Tyrosine (−1.3); Proline (−1.6); Histidine (−3.2); Glutamate (−3.5); Glutamine (−3.5); Aspartate (−3.5); Asparagine (−3.5); Lysine (−3.9); and arginine (−4.5).

The hydrophobic amino acid index is very important in imparting the interactive biological function of proteins. It is well known that substitution with an amino acid having a similar hydrophobic index can retain similar biological activities. When a mutation is introduced with reference to a hydrophobic index, the substitution is made between amino acids representing a hydrophobic index difference within ±2 in one specific example, within ±1 in another specific example, and within ±0.5 in the other specific example.

On the other hand, it is also well known that the substitution between amino acids having similar hydrophilicity values results in proteins with homogeneous biological activity. As disclosed in U.S. Pat. No. 4,554,101, the following hydrophilicity values are assigned to each amino acid residue: arginine (+3.0); Lysine (+3.0); Aspartate (+3.0±1); Glutamate (+3.0±1); Serine (+0.3); Asparagine (+0.2); Glutamine (+0.2); Glycine (0); Threonine (−0.4); Proline (−0.5±1); Alanine (−0.5); Histidine (−0.5); Cysteine (−1.0); Methionine (−1.3); Valine (−1.5); Leucine (−1.8); Isoleucine (−1.8); Tyrosine (−2.3); Phenylalanine (−2.5); Tryptophan (−3.4). When a mutation is introduced with reference to the hydrophilicity value, the substitution is made between amino acids showing a difference in hydrophilic value within ±2 in one specific example, within ±1 in another specific example, and within ±0.5 in the other specific example.

An amino acid exchange in proteins that do not entirely alter the activity of the molecule is known in the art (H. Neurath, R. L. Hill, The Proteins, Academic Press, New York, 1979). The most commonly occurring exchanges are the exchnages between amino acid residues Ala/Ser, Val/Ile, Asp/Glu, Thr/Ser, Ala/Gly, Ala/Thr, Ser/Asn, Ala/Val, Ser/Gly, Thr/Pro, Lys/Arg, Asp/Asn, Leu/Ile, Leu/Val, Ala/Glu and Asp/Gly.\

Considering the mutation having the above-mentioned biological equivalent activity, the antibody of the present invention or the nucleic acid molecule encoding the same are also interpreted to include sequences showing substantial identity with the sequences listed in the sequence listing. The above-mentioned substantial identity means a sequence exhibiting at least 61% homology, 70% homology according to one particular example, 80% homology according to another specific example, and 90% homology according to the other specific example, when aligning the sequence of the present invention with any other sequence to maximally correspond to each other, and analyzing the aligned sequence using algorithms commonly used in the art. Alignment methods for sequence comparison are well known in the art. Various methods and algorithms for the alignment are described by Smith and Waterman, *Adv. Appl. Math.* (1981) 2:482 Needleman and Wunsch, *J. Mol. Bio.* (1970) 48:443; Pearson and Lipman, *Methods in Mol. Biol.* (1988) 24: 307-31; Higgins and Sharp, *Gene* (1988) 73:237-44; Higgins and Sharp, *CABIOS* (1989) 5:151-3; Corpet et al. *Nuc. Acids Res.* (1988) 16:10881-90; Huang et al. *Comp. Appl. BioSci.* (1992) 8:155-65 and Pearson et al. *Meth. Mol. Biol.* (1994) 24:307-31. The NCBI Basic Local Alignment Search Tool (BLAST) (Altschul et al., *J. Mol. Biol.* (1990) 215: 403-10) is accessible from NBCI, and the like, and can be used in conjunction with the sequence analysis program such as blastp, blasm, blastx, tblastn and tblastx. BLSAT is accessible at www.ncbi.nlm nih.gov/BLAST/. A comparison method of sequence homology using this program can be ascertained at www.nchi.nlm.nih.gov/BLAST/blast_help.html.

According to one embodiment of the invention, the antibody of the present invention comprises a heavy chain variable region having the amino acid sequence of SEQ ID NO: 15 or SEQ ID NO: 16.

According to one embodiment of the invention, the antibody of the present invention comprises a light chain variable region having the amino acid sequence of SEQ ID NO: 17 or SEQ ID NO: 18.

The antibody of the present invention includes, but is not limited thereto, a monoclonal antibody, a multispecific antibody, a human antibody, a humanized antibody, a chimeric antibody, a short chain Fvs (scFV), a short chain antibody, Fab fragments, F(ab') fragments, disulfide-binding Fvs (dsFV) and anti-idiotype (anti-Id) antibody, and epitope-binding fragments of such antibody, and the like.

According to the present invention, the antibody of the present invention can be prepared in various forms of antibody. For example, as described in the Examples below, the antibody of the present invention can be made into Fab antibody and also can provide an antibody in the whole form by recombining constant regions derived from human with the light and heavy chain variable regions obtained in Fab antibody.

According to one embodiment of the present invention, the antibody of the present invention is a monoclonal antibody. The term "monoclonal antibody" means an antibody molecule of a single molecular composition obtained in substantially the same population of antibodies, and the monoclonal antibody exhibits a single binding specificity and affinity for a particular epitope.

The antibody of the present invention can be used to treat cancer by binding to a TM4SF5 protein known as a tumor-specific antigen and reducing/inhibiting/eliminating its activity.

Nucleic Acid Molecules and Recombinant Vectors

According to another embodiment of the present invention, the present invention provides nucleic acid molecules encoding heavy chain variable regions of said antibody or antigen-binding fragments thereof.

According to another aspect of the present invention, the present invention provides nucleic acid molecules encoding light chain variable regions of antibody for TM4SF5 or antigen-binding fragments thereof.

As used herein, the term "nucleic acid molecule" has the meaning including DNA (gDNA and cDNA) and RNA molecules, and nucleotides which are basic constituent units in nucleic acid molecule are not only natural nucleotides, but also the analogue in which sugar or base part is modified (Scheit, Nucleotide Analogs, John Wiley, New York (1980); Uhlman and Peyman, Chemical Reviews, (1990) 90:543-584). The sequences of the nucleic acids molecule encoding the heavy and light chain variable regions of the present invention can be modified. Such modifications include addition, deletion, or non-conservative substitution or conservative substitution of nucleotides.

According to one embodiment of the present invention, the nucleic acid molecules encoding the heavy chain variable regions comprise a nucleotide sequence of SEQ ID NO: 19 or SEQ ID NO: 20, and the nucleic acid molecules encoding the light chain variable regions comprise a nucleotide sequence of SEQ ID NO: 21 or SEQ ID NO: 22.

The nucleic acid molecules of the present invention are also interpreted to include nucleotide sequences that exhibit substantial identity to the nucleotide sequences described above. The above-mentioned substantial identity means a nucleotide exhibiting at least 80% homology, at least 90% homology in one specific example, and at least 95% homology in another specific example, when aligning the nucleotide sequence of the present invention so to be maximally corresponded to any other sequences, and analyzing the aligned sequence using an algorithm commonly used in the art.

According to another aspect of the present invention, the present invention provides a nucleic acid molecule comprising (a) a nucleic acid molecule encoding a heavy chain variable region of the present invention; and (b) a nucleic acid molecule encoding a light chain variable region of the invention.

The term "vector", as used herein, includes as a means for expressing a gene of interest in a host cell, plasmid vectors; cosmid vectors; and viral vectors such as bacteriophage vectors, adenovirus vectors, retroviral vectors, and adeno-associated viral vectors, and the like.

According to one embodiment of the invention, the nucleic acid molecule encoding the light chain variable region and the nucleic acid molecule encoding the heavy chain variable region in the vector of the present invention are operatively linked to the promoter.

As used herein, the term "operably linked" means a functional association between a nucleic acid expression control sequence (e.g., a promoter, signal sequence, or array of transcription factor binding site) and another nucleic acid sequence, whereby the regulatory sequence regulates transcription and/or translation of the above different nucleic acid sequences.

According to a preferred embodiment of the present invention, the recombinant vector of the present invention comprises (a) a nucleic acid molecule encoding a heavy chain variable region of SEQ. ID. NO: 25 of the Sequence Listing; and (b) a nucleic acid molecule encoding a light chain variable region of SEQ. ID. NO: 26 of the Sequence Listing.

The recombinant vector system of the present invention can be constructed through various methods known in the art, and specific methods for this are disclosed in Sambrook et al., Molecular Cloning, A Laboratory Manual, Cold Spring Harbor Laboratory Press (2001), which is incorporated herein by reference.

The vector of the present invention can typically be constructed as a vector for cloning or as a vector for expression. In addition, the vector of the present invention can be constructed by using prokaryotic cells or eukaryotic cells as hosts. For example, when the vector of the present invention is an expression vector and a prokaryotic cell is used as a host, it generally comprises a strong promoter capable of promoting transcription (e.g., tac promoter, lac promoter, lacUV5 promoter, lpp promoter, pLλ promoter, pRλ promotor, rac5 promoter, amp promoter, recA promoter, SP6 promoter, trp promoter and T7 promoter, etc.), a ribosome binding site for initiation of translation, and a transcription/translation termination sequence. When *Escherichia coli* (*E. coli*) (e.g., HB101, B121, DH5α, etc.) is used, the promoter and operator site of the *E. coli* tryptophan biosynthetic pathway (Yanofsky, C. *J. Bacteriol.* 158: 1018-1024 (1984)) and leftward promoter of phage λ (PLλ Promoter, Herskowitz, I. and Hagen, D. Ann. Rev. Genet. 14: 399-445 (1980)) can be used as a regulatory region. When the *Bacillus* bacterium is used as a host cell, the promoter of the toxin protein gene of *Bacillus thuringiensis* (*Appl. Environ. Microbiol.* 64: 3932-3938 (1998); *Mol. Gen. Genet.* 250: 734-741 (1996)) or any promoter capable of expressing in *Bacillus* bacteria may be used as a regulatory region.

Meanwhile, the recombinant vector of the present invention can be prepared by manipulating the plasmid frequently used in the art (for example, pCL, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19 etc.), phage (for example, λgt4·λB, λ-Charon, λΔz1, M13, etc.) or viruses (for example, SV40, etc.). On the other hand, when the vector of the present invention is an expression vector and the eukaryotic cell is used as a host, a promoter derived from a genome of a mammalian cell (for example, metallothionine promoter, β-actin promoter, a human hemoglobin promoter and a human muscle creatine promoter) or a promoter derived from mammalian viruses (for example, adenovirus late promoter, vaccinia virus 7.5K promoter, SV40 promoter, cytomegalovirus (CMV) promoter, tk promoter of HSV, mouse mammary tumor virus (MMTV) promoter, LTR promoter of HIV, Moloney virus promoter, the promoter of Epstein Barr virus (EBV), and the promoter of Rous Sacoma Virus (RSV)) can be used, and it generally has a polyadenylation sequence as a transcription termination sequence.

The recombinant vectors of the invention may be fused with other sequences to facilitate purification of the antibodies expressed therefrom. Fused sequences include, for example, glutathione S-transferase (Pharmacia, USA); Maltose binding protein (NEB, USA); FLAG (IBI, USA); Tag sequences such as 6× His (hexahistidine; Quiagen, USA), Pre-S1, and c-Myc; a leader sequence such as OmpA and PelB, and the like. Further, since the protein expressed by the vector of the present invention is an antibody, the expressed antibodies can be easily purified through a protein A column, and the like, without any additional sequence for purification.

On the other hand, the recombinant vector of the present invention includes an antibiotic resistance gene commonly used in the art as a selection marker, and includes, for example, resistance genes against ampicillin, gentamycin, carbenicillin, chloramphenicol, streptomycin, kanamycin, genetisin, neomycin and tetracycline.

The vectors expressing the antibodies of the present invention can be all of a vector system in which a light chain and a heavy chain are expressed simultaneously in a single vector or the vector system in which a light chain and a heavy chain are separately expressed in separate vectors. In the latter case, both vectors are introduced into host cells via co-transfomation and targeted transformation. The co-transfection is a method of simultaneously introducing each vector DNA encoding light and heavy chains into host cells, and then selecting cells expressing both light and heavy chains. Target transformation is a method carried out by selecting cells transformed with a vector comprising the light chain (or heavy chain), further transforming the selected cells expressing the light chain with a vector comprising the heavy chain (or light chain), and finally selecting a cell expressing both light and heavy chains. In the following examples, antibodies were prepared using a vector system in which light chains ($V_L$ and $C_L$) and heavy chains ($V_H$ and $C_H1$) were expressed simultaneously in a single vector.

Transformant

According to another embodiment of the present invention, there is provided a host cell transformed with the recombinant vector of the present invention.

A host cell capable of continuously cloning and expressing the vector of the present invention in a stable manner can be any host cell known in the art and includes for example, prokaryotic host cells such as *Bacillus* species strains such as *Escherichia coli, Bacillus subtilis*, and *Bacillus thuringiensis, Streptomyces, Pseudomonas* (for example, *Pseudomonas putida*), *Proteus mirabilis* or *Staphylococcus* (for example, *Staphylocus carnosus*), but is not limited thereto.

As suitable eukaryotic host cells of said vector, yeasts, such as *Aspergillus* species, *Pichia pastoris, Saccharomyces cerevisiae, Schizosaccharomyces*, and *Neurospora crassa*, other sub-eukaryotic cells, cells of higher eukaryotes such as insect-derived cells, and cells derived from plants or mammals can be used.

As used herein, "transformation" and/or "transfection" into a host cell includes any method of introducing the nucleic acids into an organism, cell, tissue or organ, and can be performed by selecting the standard techniques suitable for each of the host cells, as known to the art. Such methods include electroporation, protoplast fusion, calcium phosphate ($CaPO_4$) precipitation, calcium chloride ($CaCl_2$) precipitation, agitation with silicon carbide fibers, *Agrobacterium*-mediated transformation, PEG, dextran sulfate, lipofectamine and dry/inhibition-mediated transformation methods, and the like, but is not limited thereto.

Method for Producing anti-TM4SF5 Antibody Variants or Antigen-Binding Fragments Thereof According to another aspect of the present invention, the present invention provides a method for producing anti-TM4SF5 antibodies or antigen-binding fragments thereof, comprising: (a) culturing a host cell transformed with the recombinant vector of the present invention; and (b) expressing the anti-TM4SF5 antibodies or antigen-binding fragments thereof in the host cell, or a method for producing the antigen-binding fragment thereof.

The cultivation of the transformed host cells in the above-described preparation of antibodies can be carried out according to a suitable culture medium and culture conditions known in the art. Such a culturing process can be used by easily adjusting it according to the strain selected by those skilled in the art. These various methods of culturing are disclosed in various publications (for example, James M. Lee, *Biochemical Engineering*, Prentice-Hall International Editions, 138-176). A cell culturing is classified into an suspension culture and an adhesion culture according to the cell growth mode, and batch, infusion and continuous culture depending on the suspension culture according to a culture method. The medium used for the culture should suitably satisfy the requirements of the specific strain.

The medium comprises a variety of carbon sources, nitrogen sources and trace element components in an animal cell culture. Examples of carbon sources that may be used include carbohydrates such as glucose, sucrose, lactose, fructose, maltose, starch and cellulose, fats such as soybean oil, sunflower oil, castor oil and coconut oil, fatty acids such as palmitic acid, stearic acid, and linoleic acid, alcohols such as glycerol and ethanol, and organic acids such as acetic acid. These carbon sources may be used alone or in combination. Examples of nitrogen sources that can be used include organic nitrogen sources such as peptone, yeast extract, gravy, malt extract, corn steep liquor (CSL) and soybean wheat and inorganic nitrogen sources such as urea, ammonium sulfate, ammonium chloride, ammonium phosphate, ammonium carbonate and ammonium nitrate. These nitrogen sources may be used alone or in combination. The medium may include potassium dihydrogenphosphate, dipotassium hydrogenphosphate and the corresponding sodium-containing salts as a source of phosphorus. It may also include metal salts such as magnesium sulfate or iron sulfate. In addition, amino acids, vitamins, suitable precursors, etc. may be included.

During culturing, compounds such as ammonium hydroxide, potassium hydroxide, ammonia, phosphoric acid and sulfuric acid can be added to the culture in a suitable manner to adjust the pH of the culture. In addition, foaming can be suppressed by using a defoaming agent such as fatty acid polyglycol ester during the culture. In addition, oxygen or oxygen-containing gas (for example, air) is injected into the culture to maintain the aerobic state of the culture. The temperature of the culture is usually 20° C. to 45° C., preferably 25° C. to 40° C.

The antibodies obtained by culturing the transformed host cells can be used in an unpurified state, and further purified by high purity using various conventional methods, for example, dialysis, salt precipitation, chromatography and the like. Among them, the method using the chromatography is most widely used. The type and order of the column can be selected from an ion exchange chromatography, size exclusion chromatography, affinity chromatography, and the like, depending on the characteristics of the antibodies, the culturing method, etc.

A Pharmaceutical Composition for the Prevention or Treatment of Cancer

According to another aspect of the present invention, the present invention provides a pharmaceutical composition for preventing and treating the cancer, comprising (a) a pharmaceutically effective amount of antibodies for TM4SF5 of the present invention or antigen-binding fragments thereof; and (b) a pharmaceutically acceptable carrier.

These antibodies can bind to TM4SF5 with high affinity to inhibit the growth, invasion and metastasis of cancer expressing TM4SF5, and thus can be used for the prevention and treatment of cancer alone or with a conventional pharmaceutically acceptable carrier.

As used herein, the term "prevention" means any act that inhibits or slows the progress of cancer by administration of the composition of the present invention, and "treatment" means an inhibition of cancer development, reduction of cancer or an elimination of cancer.

According to one embodiment of the present invention, cancer which is a disease to be applied to the composition of the present invention is a cancer expressing TM4SF5, and examples of such cancer include liver cancer, colon cancer, pancreatic cancer, lung cancer, gastric cancer, rectal cancer, soft-tissue sarcoma, colorectal cancer, carcinoma of the papilla vateri, nonendocrine lung tumor, bronchial carcinoid tumor, etc.

The pharmaceutically acceptable carriers to be included in the pharmaceutical composition of the present invention are those conventionally used in the preparation and include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, etc., but is not limited thereto. The pharmaceutical composition of the present invention may further include a lubricant, a wetting agent, a sweetener, a flavoring agent, an emulsifying agent, a suspending agent, a preservative, etc., in addition to the above components. Suitable pharmaceutically acceptable carriers and formulations are described in detail in Remington's Pharmaceutical Sciences (19th ed., 1995).

The pharmaceutical composition of the present invention can be administered orally or parenterally, and in the case of parenteral administration, it can be administered by intravenous injection, subcutaneous injection, muscle injection, intraperitoneal injection, endothelial administration, topical administration, intranasal administration, intrapulmonary administration, intrarectal administration, etc. When administered orally, the proteins or peptides are digested so that the oral composition should be formulated to coat the active agent or protect it from degradation at the stomach. The pharmaceutical composition may also be administered by any device capable of transferring the active agent to the target cell.

The appropriate dosage of the pharmaceutical composition of the present invention varies depending on factors such as the formulation method, administration mode, age, body weight, sex, pathological condition of the patient, food, administration time, administration route, excretion rate and responsiveness, and it can be easily determined and prescribed by a skilled physician as the dosages that are effective for the desired treatment or prophylaxis. According to one embodiment of the present invention, the daily dosage of the pharmaceutical composition of the present invention is 0.0001-100 mg/kg. As used herein, the term "pharmaceutically effective amount" means an amount sufficient to prevent or treat cancer.

The pharmaceutical composition of the present invention may be prepared into a unit dosage format by formulating by using a pharmaceutically acceptable carrier and/or excipient, according to a method which can be easily carried out by those having ordinary skill in the art to which the present invention belongs, or may be prepared by encorporating it into a multi-dose container. In this case, the formulations may be in the form of solutions, suspensions or emulsions in oils or aqueous media, or in the form of extracts, powders, suppositories, powders, granules, tablets or capsules, and may additionally contain dispersing or stabilizing agents.

The composition of the present invention may be administered as an individual therapeutic agent or in combination with other therapeutic agents, and may be administered sequentially or simultaneously with conventional therapeutic agents.

Antibodies can be injected into vivo in the form of antibody-therapeutic conjugates and used to treat cancer. Therapeutic agents include chemotherapeutic agents, radionuclides, immunotherapeutic agents, cytokines, chemokines, toxins, biological agents, enzyme inhibitors, etc. Preferred functional molecules for coupling to antibodies or fragments thereof of the invention are chemicals, cytokines or chemokines. The chemical is an anticancer agent and may be selected from the group consisting of, for example, asibaiicin, aclarubicin, acordazole, acronisin, adozelesin, alanosin, aldosterukin, allopurinol sodium, altretamine, aminogjutethimide, amonafide, ampligen, amsacrine, androgens, anguidine, amidicolline glycinatem, asalay, asparaginase, 5-azacytidine, azathioprine, bacillus calmette-guerine (BCG), Baker's antipol, beta-2-dioxythioguanosine, bisanthrene HCl, bleomycin sulfate, bulsulphane, buthionine sulfoximine, BWA773U82, BW 502U83/HCl, BW 7U85 mesylate, ceracemide, carbetimor, carboplatin, carmustine, chlorambusyl, chloroquinoxaline-sulphonamide, chlorozotocin, cromomycin A3, cisplatin, cladribine, corticosteroid, Corynebacterium parbium, CPT-11, crysnatol, cyclocytidine, cyclophosphamide, cytarabine, cytemvena, dabis maleate, decarbazine, dactinomycin, daunorubicin HCl, diazauridine, dexlazonic acid, dianhydro galactitol, diaziquone, dibromodulcitol, didemine B, diethyldithiocarbamate, diclycoaldehyde, dihydro-5-azacytin, doxorubicin, etchinomycin, dodatrexate, edelphosine, eprolnitin, elliosse solution, elsamitrucin, epilubicin, esolubicin, estramustine phosphate, estrogen, etanidazole, ediophos, etophoside, fadrazol, fazarabin, fenletinide, filgramstim, finasteride, flavone acetic acid, floxuridine, fludarabine phosphate, 5'-fluorouracil, Fluosol™, flutamide, gallium nitrate, gemcitabine, gossyrelin acetate, hepsulfam, hexamethylene bisacetamide, homoharingtonin, hydrazine sulfate, 4-hydroxyandrostenedion, hydroxyurea, idarubicin HCl, iphosphamide, 4-ipomeanol, iproflatine, isotretinoin, leucovorin calcium, leuprolide acetate, levamisol, liposome daunorubicin, liposome capture doxorubicin, lomerstine, lonidamine, mytansin, mechloretamine hydrochloride, melphallan, menogaril, merbaron, 6-mercaptopurine, mesna, methanol extract of bacillus callete-guerin, methotrexate, N-methylformamide, mifepristone, mitoguazone, mitomycin-C, mitotan, mitoxanthrone hydrochloride, monocyte/macrophage colony-stimulating factor, navilone, Napoxidine, neocarginostatin, octreotide acetate, ormaflatin, oxaliplatin, paclitaxel, palla, pentostatin, piperazinedione, pipobroman, pirarubicine, piritrexim, pyroxantrone hyhydrochloride, PIXY-321, plicamycin, porphymer sodium, prednimustine, procarbazine, progestins, pyrazofurin, razoxane, sargramostim, semustin, spirogermanium, spiromustine, streptonygrin, streptozocin, sulophener, suramin sodium, tamoxifen, taxotere, tegafur, teniphoside, terephthalamidine, teroxiron, thioguanine, thiotepa, thymidine injection, thiazopurine, topotecan, toremifene, tretinoin, trifluoperazine hydrochloride, trifluridine, trimetrexate, tumor necrosis factor (TNF), uracil mustard, vinblastine sulfate, vincristine sulfate, vindesine, vinorelbine, binzolidine, Yoshi 864, zorubicin, cytosine arabinoside, etoposide, melphalan, taxotel, taxol, and a mixture thereof, but are not limited thereto.

Composition for Diagnosing a Cancer

According to still another aspect of the present invention, there is provided a kit for diagnosing cancer, comprising the above-mentioned antibodies or antigen-binding fragments thereof of the present invention.

The antibodies of the present invention can be applied to biological samples to diagnose the onset of cancer.

As used herein, the term "biological sample" may refer to a tissue, cell, whole blood, serum, plasma, tissue autopsy sample (brain, skin, lymph node, spinal cord, etc.), cell culture supernatant, ruptured eukaryotic cell, bacillus expression system, etc., but is not limited thereto. These biological samples can be reacted with the antibodies of the present invention without any manipulation or manipulation to confirm the onset of cancer.

The formation of the above-described antigen-antibody complex can be detected by a variety of methods including colormetric method, electrochemical method, fluorimetric method, luminometry, particle counting method, visual assessment, or scintillation counting method. As used herein, "detection" is intended to detect antigen-antibody complexes and can be carried out using various markers. Specific examples of the label include an enzyme, a fluorescein, a ligand, a luminescent material, a microparticle or a radioactive isotope.

Examples of the enzyme used as the detection label include acetylcholinesterase, alkaline phosphatase, β-D-galactosidase, horseradish peroxidase, β-Lactamase, and the like; examples of the fluorescent agent include $Eu^{3+}$, $Eu^{3+}$ chelate, cryptate, and the like; examples of the ligand include a biotin derivative and the like; examples of the luminescent material include an acridinium ester, an isoluminol derivative, and the like; examples of the fine particles include colloidal gold and colored Latex, and the like; and the radioactive isotopes include $^{57}$Co, $^3$H, $^{125}$I, $^{125}$I-Bonton Hunter reagents, and the like.

According to one embodiment of the invention, the antigen-antibody complex can be detected using enzyme-linked immunosorbent assay (ELISA). Enzyme-linked immunosorbent assays include various ELISA methods, such as direct ELISA using labeled antibody that recognizes antigen attached to a solid support, indirect ELISA using labeled secondary antibodies that recognize capture antibody in complex of antibody that recognizes an antigen attached to a solid support, a direct sandwich ELISA using another labeled antibody that recognizes an antigen in the complex of antibody and antigen attached to the solid support, an indirect sandwich ELISA using the labeled secondary antibody that recognizes the antibody obtained after reacting another antibody that recognizes the antigen in a complex of antibody and antigens attached to the solid support, etc. The antibodies of the present invention can have a detection label, and when not having a detection label, it can be identified by treating another antibody that can capture the antibodies of the present invention and have a detection label.

Advantageous Effects

As can be seen through the present invention, immunization of cyclic peptide vaccines and injection with TM4SF5-specific antibodies have anti-metastatic effects on colon cancer in a mouse model, and can also be used as a starting platform for applying in the treatment of patients.

BRIEF DESCRIPTION OF DRAWINGS

FIG. 1 shows the induction of antibodies in mice immunized with the TM4SF5 cyclic peptides vaccine. (A) Sequences of TM4SF5 target site. (B) Sequences of the peptides used in the present invention. hTM4SF5EC2-C and mTM4SF5EC2-C represent cyclic peptides of hTM4SF5EC2 and mTM4SF5EC2 linked by disulfide bonds. (C) BALB/c mice (n=5/group) were injected with PBS or hTM4SF5EC2-C peptide and Lipoplex(O) complex three times at 10-day intervals. Titer and reactivity of the antibody in serum were measured by ELISA using the peptides as described. (D) Isotypes of antibodies that respond to hTM4SF5EC2-C peptides are identified by ELISA for isotyping.

FIG. 2 shows the inhibition of lung metastasis by immunization with the TM4SF5 cyclic peptide vaccine in a heterologous transplantation colon cancer model. BALB/c mice (PBS control n=8, colon caner cell group n=15) were injected with PBS, Lipoplex (O), hTM4SF5EC2-C peptides and CpG-DNA (Lipoplex (O)) complex encapsulated in DOPE:CHEMS three times at 10-day intervals. Transition models were established by transplanting CT-26 cells into treated BALB/c mice and the mouse body weight and survival were investigated. (A) Experimental schedule. (B) Body weight was measured every 2 days for 20 days after CT-26 cell transplantation. (C) Survival of the immunized mice after CT-26 cell transplantation. (D) Macroscopic appearance of the lung examined on day 52. (E) The weight of the mouse lung on day 52. *P<0.05. (F) Histological examination of lung tissue. Scale bar, 100 μm.

FIG. 3 represents the decrease in the number of pulmonary nodules by immunization with the TM4SF5 cyclic peptide vaccine in a heterotypic implant-colon cancer model. BALB/c mice were injected with PBS or hTM4SF5EC2-C peptides and Lipoplex (O) complex (n=8/group) three times at 10-day intervals. The metastasis model was established by implanting CT-26 cells in treated BALB/c mice and tumor growth was monitored for 46 or 50 days. (A) Experimental schedule. (B) Macroscopic appearance and lung weight of lung irradiated on day 46 (CT-26 group) and 50 days (PBS control, Lipoplex (O)+ hTM4SF5EC2-C peptides/CT-26 group (n=4/each group). (C) Number of pulmonary nodules at 46 days (CT-26 group) and 50 days (PBS control, Lipoplex (O)+hTM4SF5EC2-C peptides/CT-26 group (n=4/each group) **P<0.01.

FIG. 4 represents screening of hybridoma clones in HAT medium producing anti-TM4SF5 monoclonal antibodies recognizing TM4SF5 cyclic peptides. (A) Three BALB/c mice were immunized ip (intraperitoneal) with hTM4SF5EC2-C peptides and MB-ODN 4531 (O) co-encapsulated in DOPE:CHEMS complex four times at 10-day intervals, the serum was collected and then total IgGs were assayed using an ELISA kit. (B, C) ELISA results derived from initial screening of cell-fusion experiments in HAT medium using spleen cells of the mice immunized with hTM4SF5EC2-C peptides. (D) HEK 293F-EV (empty vector) and proteins of HEK 293F-TM4SF5 cells were separated by SDS-PAGE and analyzed by Western blot using hybridoma clone (H1 clone of B) culture supernatant and anti-Myc antibody.

FIG. 5 shows screening of hybridoma clones in HT medium producing anti-TM4SF5 monoclonal antibodies recognizing TM4SF5 cyclic peptides. (A, B) The hybridoma clones derived from FIG. 5 were selected for the production of monoclonal antibodies, and were subcloned using the limiting dilution method. (C) Analysis of hybridoma clone culture supernatants for cyclic peptides hTM4SF5EC2-C using ELISA. (D) HEK 293F-EV (empty vector) and proteins of HEK 293F-TM4SF5 cells were separated by SDS-PAGE and analyzed by Western blot using hybridomarker culture supernatant.

FIG. 6 represents purification and characterization of mouse anti-TM4SF5 monoclonal antibodies recognizing TM4SF5 cyclic peptides. (A) Hydrops abdominis was producted from BALB/c mice by injecting i.p. into the abdominal cavity with hybridoma clone (2A10 clone) derived from FIG. 5. Anti-TM4SF5 monoclonal antibody was purified using protein-A agarose column chromatography and the purified antibody was identified by SDS-PAGE and Coomassie blue staining. (B) The isotype was determined by obtaining titration curves using purified monoclonal antibodies. (C) A binding affinity of monoclonal antibody for cyclic peptide hTM4SF5EC2-C was determined by using ELISA. (D) A binding affinity of monoclonal antibody for cyclic peptide hTM4SF5EC2-2 was determined by using Reichert Analytical Instruments SPR 7500DC (Reichert). Biotinylated peptides were immobilized on streptavidin chip and the amount of antibody was increased. Kinetic parameters of binding reactions are expressed under sensorgrams. (E) HEK 293F-EV (empty vector) and proteins from HEK 293F-TM4SF5 cells were separated by SDS-PAGE and analyzed by Western Blot using anti-TM4SF5 monoclonal antibody (mEC2-C), anti-Myc antibody or anti-β-actin antibody. HEK 293F-EV and proteins of HEK 293F-TM4SF5 cell were immunoprecipitated with mEC2-C and analyzed by Western blot using anti-Myc antibody. These results are representative of at least three independent experiments.

FIG. 7 shows the therapeutic effect of anti-TM4SF5 monoclonal antibody against colon cancer growth in a xenograft mouse model. Mouse tumor models were established by implanting HT-29 cells into BALB/cAnNCri-nu/ nu mice. PBS or anti-TM4SF5 monoclonal antibody was injected into the mice when the tumor size reaches 5 mm in diameter and the tumor growth was monitored for 31 days (n=6 each). (A) Experimental schedule. (B) Macroscopic appearance of colon cancer tissue. (C) Tumor volume (width$^2$×length/2). (D) Tumor weight. (E) Weight.

FIG. 8 is a cDNA sequence of the heavy and light chain variable regions isolated from a hybridoma cell clone. (A) the sequence of the heavy chain variable domain. (B) the sequence of the light chain variable domain. The predicted amino acid sequence is displayed at the bottom of the cDNA sequence.

FIG. 9 shows the figure obtained by analyzing the sequence for the construction of humanized antibodies and arranging in a straight line the variable heavy chain and the variable light chain divided from amino acid sequences for HEC2-C-1, hEC2-C-2, the humanized antibodies of the present invention; mEC2-C, antibody derived from wild-type mouse; Herceptin antibody with human VH3-Vk1 subtype framework used in establishing the humanized antibody. The square brackets ([ ]) indicate the respective CDR region, the underlined letters indicate the amino acids corresponding to the Vernier region, and the asterisk (*) indicates the part reverse-replaced with the amino acid derived from the mouse mEC2-C wild type antibody. At this time, the CDR region was defined according to Kabat numbering.

FIG. 10 shows a front view and a top view for the result superimposing the variable regions (Fv) of the mEC2-C, hEC2-C-1 and hEC2-C-2 antibodies shown in FIG. 9 by computer remodeling them in the Pymol software, respectively, so as to review the change of the structure after implanting CDR. The skeletal region (FR) is expressed in black and white, the CDR of each antibody is represented by the same color as the color shown in the figure, and each CDR of the heavy chain is represented by HCDR1/2/3 and each CDR of the light chain is represented by LCDR1/2/3.

FIG. 11: Purification and characterization of humanized anti-TM4SF5 monoclonal antibodies recognizing TM4SF5 cyclic peptides. (A) Humanized Anti-TM4SF5 antibodies were purified using protein-A agarose column chromatography and the purified antibodies were identified by SDS-PAGE and Coomassie blue staining. (B) Analysis of binding affinities of humanized antibodies to cyclic peptide hTM4SF5EC2-C using ELISA. (C) Analysis of humanized antibodies binding affinity for cyclic peptides hTM4SF5EC2-C using Reichert Analytical Instruments SPR 7500DC (Reichert). (D) Proteins from HEK 293F-EV and HEK 293F-TM4SF5 cells were separated by SDS-PAGE and analyzed by Western blot using anti-TM4SF5 antibody (hEC2-C-2) or anti-β-actin antibody. Protein homogenate of HEK 293F-EV and HEK 293F-TM4SF5 cells was immunoprecipitated with hEC2-C-2 and analyzed by Western blot using anti-Myc antibody.

FIG. 12 shows the effect of humanized anti-TM4SF5 monoclonal antibody on migration of colon cancer cells. (A) Moving Assay. Scale bar, 100 μm. (B) Wound healing assay. Scale bar, 300 μm. The movement property of CT-26 and HCT-116 cells was analyzed after treating them with PBS, normal human IgG, or hEC2-C-2 antibodies. These results are representative of at least three independent experiments. *P<0.05, ***P<0.001.

FIG. 13 shows the effect of humanized anti-TM4SF5 antibodies on the expression of adhesion molecules. (A) CT-26 and HCT-116 cells were treated with PBS, normal human IgG, or hEC2-C-2 antibodies and expression of E-cadherin and β-catenin was analyzed with anti-E-cadherin and anti-β-catenin antibodies by confocal microscopy. a scale bar, 20 μm. (B) Western blot analysis. β-actin expression level was used as a loading control. Expression of E-cadherin and β-catenin was determined using anti-E-cadherin and anti-β-catenin antibodies. Band intensity was measured and quantitative changes were shown in graph. These results are representative of at least three independent experiments.

FIG. 14 shows the therapeutic effect of injected humanized anti-TM4SF5 monoclonal antibodies against HCC tumor growth in a xenograft mouse model. Mouse tumor models were established by implanting Huh-7 cells into BALB/cAnNCri-nu/nu mice. PBS or humanized anti-TM4SF5 antibodies are injected into mice when the tumor size reaches 5 mm in diameter, and their tumor growth is monitored for 44 days (n=6 each). (A) Experimental schedule. (B) Macroscopic appearance of HCC tumor tissue. (C) Tumor volume (width$^2$×length/2). (D) Tumor weight. (E) Weight.

FIG. 15 shows the therapeutic effect of humanized anti-TM4SF5 monoclonal antibodies against colon cancer growth in a xenograft mouse model. Mouse tumor models were established by implanting HT-29 cells into BALB/cAnNCri-nu/nu mice. PBS or humanized anti-TM4SF5 antibodies are injected into mice when tumor size reaches 5 mm in diameter, and their tumor growth is monitored for 28 days (n=6 each). (A) Experimental schedule. (B) Macroscopic appearance of colon cancer tissue. (C) Tumor volume (width$^2$×length/2). (D) Tumor weight. (E) Weight.

FIG. 16 represents the survival rate of lung metastasis by humanized anti-TM4SF5 monoclonal antibody in a allogeneic colon cancer model. CT-26 cells were injected intravenously into BALB/c mice. PBS, human IgG or hEC2-C-2 were intravenously injected into the mice and tumor growth was monitored for 22 days (PBS control n=8, cancer cell group each n=12). (A) Experimental schedule. (B) Body weight was measured every 2 day for 20 days. (C) Survival of humanized anti-TM4SF5 antibodies-injected mice after transplantation of CT-26 cells.

FIG. 17 shows inhibition of lung metastasis by humanized anti-TM4SF5 monoclonal antibodies in a allogeneic colon cancer model. CT-26 cells were injected intravenously into BALB/c mice. PBS, human IgG or hEC2-C-2 was intravenously injected into the mice and tumor growth was monitored after 19 days (PBS control n=8, cancer cell group n=12 each). (A) Experimental schedule. (B) Examination of the shape of the lung on day 19. (C) The lung weight of the mouse on day 19. **P<0.01. (D) Histological examination of lung tissue. Scale bar: 100×, 100 μm; 400×, 25 μm.

BEST MODE FOR INVENTION

Hereinafter, the present invention will be described in more detail with reference to Examples. It is will be self-evident to those skilled in the art that these Examples are only for illustrating the present invention in more detail and that the scope of the present invention is not limited by these Examples in accordance with the gist of the present invention.

Example 1

Synthesis of Cyclic Peptides of CpG-DNA and hTM4SF5EC2

The natural CpG-DNA consisting of 20 bases with three CpG motifs, MB-ODN 4531 (O) (Kwon S, Kim D, Park B K, Cho S, Kim K D, Kim Y E, Park C S, Ahn H J, Seo J N, Choi K C, Kim D S, Lee Y, Kwon H J. PLoS One. 2012; 7(3):e331214) was received from Samchullypharm, Co, Ltd. MB-ODN 4531 is consisted of 20 bases with three CpG motifs: AGCAGCGTTCGTGTCGGCCT (SEQ ID NO: 23). The present inventors designed cyclic peptides (hTM4SF5EC2-C, FIG. 1B) that mimicked extracellular domain 2 of human TM4SF5 and purchased the chemically synthesized cyclic peptides and control peptides from Peptron, Co., Ltd.

Example 2

Preparation of Liposome Complexes Co-Encapsulating Cyclic Peptides Epitope and CpG-DNA with TM4SF5 Targeting Peptides Vaccine Liposome complexes were consisted of TM4SF5 cyclic peptides (hTM4SF5EC2-C) and CpG-DNA co-encapsulated with DOPE:CHEMS (Lipoplex (O)), and were prepared as reported on Kwon S, Kim D, Park B K, Cho S, Kim K D, Kim Y E, Park C S, Ahn H J, Seo J N, Choi K C, Kim D S, Lee Y, Kwon H J. PLoS One. 2012; 7(3): e331214.

Example 3

Animals

Female BALB/c mice and BALB/cAnNCri-nu/nu mice (4 weeks old) were purchased from Nara Biotech, Inc. and the mice were kept at 20-25° C. and 32-37% humidity under unspecified hospital conditions. All animal testing procedures were followed by the National Veterinary Research and Quarantine Service's Guide of Laboratory Animal Use Management and were performed under the approval of the Animal Experimentation Committee of Hallym University. We sacrificed mice under isoflurane inhalation and made every effort to minimize pain.

Example 4

Antigen-Specific Ig Enzyme-Linked Immunosorbent Assays (ELISA)

Mice were sacrificed before and 10 days after each administration to obtain serum. To determine the total IgG titer and amount, a 96-well immunoplate (Nalgen Nunc International) was coated with 5 µg/ml hTM4SF5EC2-C cyclic peptide and blocked with 0.05% PBST containing 1% BSA for two hours. After removal of blocking solution, 100 µl of the culture supernatant was added and incubated for 2 hours at room temperature, then washed with PBST and incubated for 2 hours with the detection antibody such as horseradish peroxidase (HRP)-bound an anti-IgG antibody. Colorimetric assays were developed with TMB substrate solutions and absorbance was measured at 450 nm using a Spectra Max 250 microplate reader.

To determine IgG isotype, 96-well immunoplates were coated with hTM4SF5EC2-C peptides, reacted with serum and incubated with HRP-conjugated anti-mouse IgG (each isotype) antibody (BD Biosciences).

Example 5

Evaluation of TM4SF5 Peptides Vaccine as Anti-Metastasis Agent in Lung Metastasis Model of Colorectal Cancer Liposome complexes composed of TM4SF5 cyclic peptides (hTM4SF5EC2-C) co-encapsulated with DOPE:CHEMS (Lipoplex (O)) comprising CpG-DNA were immunized three times at 10-day intervals in BALB/c mice. Control mice were injected with PBS or Lipoplex (O). For metastatic cancer animal experiments, mice were intravenously injected with CT-26 mouse colon cancer cell line (PBS control n=8, colon cancer cell group n=15) at $1\times10^5$ cells at 30 days. Body weight was measured at 2-day intervals. On day 22 after CT-26 cell injection, the mice were sacrificed and the lung weight was measured.

Example 6

Investigation of Pulmonary Nodules

BALB/c mice were immunized as above and injected with CT-26 cells. At twenty days after CT-26 cell injection, the mice were sacrificed, the cannula was inserted into the organs with a 20-gauge catheter and 1 ml of Indian ink (Parker, 1:16 diluted with PBS) was injected into the lungs. The lungs were extracted, soaked in Fekete's solution, decolored, and then counted for metastatic nodules (Larive R M, Moriggi G, Nat Commun. 2014; 5: 3881).

Example 7

Production of Mouse Monoclonal Antibodies Specific for TM4SF5

HTM4SF5EC2-C cyclic peptides ($^{131}$TACAY-LLNRTLWDRCEAPPRVVPWNCT157) of the human TM4SF5 (hTM4SF5) proteins were prepared using an automated peptide synthesizer (Peptron III-R24, Peptron) in Peptron, Co., Ltd.

Female BALB/c mice were intraperitoneally injected with hTM4SF5EC2-C cyclic peptides co-encapsulated with DOPE:CHEMS complex containing CpG-DNA four times at 10-day intervals. After splenocytes were obtained from the immunized spleen, they were fused with HAT-sensitive SP2/0 mouse myeloma cells under the presence of 40% (w/v) polyethylene glycol according to the standard hybridoma technique (Yokoyama W M, et al. *Curr Protoc Immunol* Chapter 2, Unit 2.5 (2006)). The culture supernatant of the hybridoma cells was tested by ELISA to confirm binding to hTM4SF5EC2-C cyclic peptides, and positive hybridoma groups were screened. ELISA-positive hybridoma cell lines were subcloned and then injected into the abdominal cavity of BALB/c mice to generate ascites. Anti-TM4SF5 monoclonal antibodies (mEC2-C) were purified from the ascites using protein A column chromatography (Amersham Pharmacia Biotech).

Example 8

SPR (Surface Plasmon Resonance) Analysis

The affinities of anti-hTM4SF5 monoclonal antibody (mEC2-C) and humanized anti-TM4SF5 antibody (hEC2-

C-2) binding to hTM4SF5EC2-C cyclic peptide were measured at 25° C. using the Reichert SPR system. Biotinylated peptides were captured from each flowing cell surface of a streptoavidin-coated sensor chip. Biotin was used as a negative control. Anti-hTM4SF5 monoclonal antibody (mEC2-C) and humanized anti-TM4SF5 antibody were injected at a flow rate of 30 ml/min. Data were evaluated using Reichert SPR evaluation software.

Example 9

Cell Culture

Human HCC cell line such as Huh7, and human colon cancer cell lines such as HT-29 and HCT116, and mouse colon cancer cell line CT-26 were obtained from Korean Cell Line Bank. CT-26 cells were maintained in DMEM containing 10% fetal bovine serum (FBS; Hyclone), 2 mM glutamine, 100 U/ml penicillin and 100 ug/ml streptomycin. Other cell lines were maintained in RPMI 1640 medium containing 10% FBS, 25 mM HEPES, 100 U/ml penicillin and 100 ug/ml streptomycin. All cells were incubated at the temperature of 37° C. in 95% air and 5% $CO_2$.

Example 10

Recombinant Human TM4SF5 Expression

Human TM4SF5 cDNA was amplified by RT-PCR from Huh-7 mRNA using the following primer set: hTM4SF5 5' primer, 5'-CTCGAGATGTGTACGGGAAAATGTGCC-3' (SEQ ID NO: 24), hTM4SF5 3' primer, 5'-AAGCTTTTGT-GAGGTGTGTCCTGTTTTTT-3' (SEQ ID NO: 25). The cDNA fragment was cloned into the expression vector pcDNA-3.1/Myc-His(−)B (Invitrogen). HEK 293F cells ($1 \times 10^6$ cells/ml) were transfected with 2.5 µg/ml hTM4SF5/pcDNA and 7.5 µg/ml polyethylenimine (PEI, Polysciences) for the production of stable cell lines expressing hTM4SF5, and the transfected cells were collected using 500 µg/ml G418 (Calbiochem) for 14 days. Expression of Myc-tagged hTM4SF5 was confirmed by Western blot analysis using anti-Myc-tag antibodies.

Example 11

Western Blot and Immunoprecipitation Analysis

In order to analyze the specificity of anti-TM4SF5 monoclonal antibody and humanized anti-TM4SF5 antibody, TM4SF5-overexpressed cell lysates were separated on SDS-PAGE, and Western blot and immunoprecipitation assays were performed as described on Kwon S, Kim D, Rhee J W, Park J A, Kim D W, Kim D S, Lee Y, Kwon H J. BMC Biol. 2010; 8:23. In order to identify the expression of E-cadherin and β-catenin in humanized anti-TM4SF5 antibody-treated cells, cell lysates were analyzed with SDS-PAGE and Western blotting method as descried in Kwon S, Choi K C, Kim Y E, Ha Y W, Kim D, Park B K, Wu G, Kim D S, Lee Y, Kwon H J. Cancer Res. 2014; 74(14):3844-3856.

Example 12

Colon Cancer Mouse (Xenotransplantation) Model for Mouse Anti-TM4SF5 Monoclonal Antibody Twelve BALB/cAnNCri-nu/nu mice were subcutaneously injected with $5 \times 10^6$ HT-29 cells containing 50% matrigel (BD biosciences) on the dorsal right flank. When the tumor diameter reached 5 mm, the mice were randomly sorted into two treatment groups (6 mice/each group) of PBS and anti-TM4SF5 monoclonal antibody (mEC2-C). Antibodies (25 mg/kg) were injected into the tail vein twice a week. During 30 days after injecting the cancer cell, the tumor diameter was measured per 3 or 4 day-interval, and the tumor volume was calculated according to an equation $Width^2 \times length/2$. When the tumor size is reached ±600 $mm^3$, BACB/cAnNCri-NCri-nu/nu mice were sacrificed, and the tumor weight was measured.

Example 13

Cloning of the Variable Heavy and Light Chains (Fabs) of Anti-TM4SF5 Monoclonal Antibody Hybridoma cells producing anti-TM4SF5 monoclonal antibodies (mEC2-C) were cultured, total RNAs were extracted from hybridoma cells, and cDNA were synthesized by reverse transcription. To clone the Fab sequence of anti-TM4SF5 monoclonal antibodies, the resulting cDNAs were amplified using Vent polymerase (NEB) and the following primers: Heavy chain primers, IGG3: GGAA-GATCTAGGGACCAAGGGATAGACAGATGG, 5'MH2: CTTCCGGAATTCSARGTN-MAGCTGSAGSAGTCWGG; Kappa chain primers, 3'Kc: GGTGCATGCGGATACAGTTGGTGCAGCATC, 5'Mk: GGGAGCTCGAYATTGTGMTSACMCARWCTMCA. Standard PCR reactions were performed for 25 cycles. The PCR product was ligated directly into the pGEM-T isotype vector (Promega). Cloned mouse Ig inserts were analyzed by DNA sequencing.

Example 14

Sequence Analysis and Molecular Modeling of Variable Fragment (Fv)

Immunoglobulin variable domain sequences of mEC2-C were analyzed with IgBLAST (http://www.ncbi.nlm.nih-.gov/igblast/)(Ye J, Ma N, Madden T L, Ostell J M. IgBLAST: Nucleic Acids Res. 2013; 41 (Web Server issue): W34-4027). Six complementarity determining regions (CDRs) were determined by Kabat numbering (Kabat E A, Wu T T. J Immunol. 1991; 147 (5): 1709-171928), and some framework (FR) residues of mEC2-C mAb were inserted as human VH3-Vk1 subfamily (in this case, the Herceptin framework). Three-dimensional structures of mouse and humanized EC2-C Fv amino acid sequences were simulated using a web modeling program, ROSIE (Lyskov S, Chou F C, Conchuir S O, Der B S, Drew K, Kuroda D, Xu J, Weitzner B D, Renfrew P D, Sripakdeevong P, Borgo B, Havranek J J, Kuhlman B, et al. PLoS One. 2013; 8(5): e6390629). This program identifies most homologous templates for heavy and light chain FRs and CDRs and combines this template structures into optimized models. As a result, the model structure was superimposed by ribbon model using Pymol software (DeLano Scientific LLC).

Example 15

Construction of Humanized Antibodies Against EC2-C Peptides Antigens Determination of CDRs of Non-Human (Mouse) Derived Antibodies For humanization, it is first necessary to determine the CDRs of the antibodies. Methods for determining CDRs include Kabat numbering based on the diversity of amino acid sequences, Chothia numbering based on the structure of the loop region (James et al., January; 42: D1140-6, 2014) IMGT numbering based on the high degree of conservation of variable region structures (Lefranc M P et al., Front Immunol., 5; 5: 22, 2001), etc., and Kabat numbering is most widely used. CDRs of mouse-derived antibodies to the EC2-C peptide antigens were determined according to Kabat numbering (see FIGS. 8 and 9).

Selection of Human Antibodies Framework Suitable for Construction of Humanized Antibodies and CDR Region Transplantation of Wild Type Antibodies The variable regions of human antibody are broadly classified according to the amino acid sequence into 7 subtypes (VH1, VH2, VH3, VH4, VH5, VH6, VH7) for the heavy chain and 17 subtypes (κ1,κ2,κ3,κ4,κ5,κ6,λ1,λ2,λ3, λ4,λ5,λ6,λ7,λ8,λ9,λ10,λ11) for the light chain. Because each subtype has a different amino acid sequence, it has a different biologic structure and thus has a different stability, and thus the frequency used in natural human antibodies repertoire also varies (Tiller T et al., MAbs, 5(3):445-70, 2013). Generally, when humanized antibodies are prepared using CDR grafting method, in order to maintain the structure of CDR as much as possible, while they are transferred to a human framework having high sequence homology with wild type non-human derived antibodies, in this case, the subtypes of humanized antibodies is naturally stable, but there is a possibility that antibodies with low stability can be obtained after humanization.

In order to determine the human framework suitable for the humanization of the mouse-derived antibody to the hTM4SF5EC2-C peptide antigen, we searched subtypes of the variable regions of human antibody with the most high sequence homology to the existing wild type antibody through Igblast (URL: http://www.ncbi.nlm.nih.gov/igblast/) and as a result, found that they have the most homology with subtypes of VH4 and Vk4 of human antibody. However, according to the reference, each of the above two subtypes is very low on frequency and stability which are found in naturally occurring human antibody repertoires. Therefore, in order to construct a highly stable humanized antibody while maintaining the affinity for the antigen and its function, an antigen binding site was transplanted into the human antibodies framework of the VH3-Vk1 subtype. The VH3-Vk1 subtype is the framework of a commercialized therapeutic antibody (Herceptin), and its thermodynamic stability and expression yield have been well verified by previous studies and in particular, have been used successfully for the humanization of various mouse antibodies (Carter et al., Proc Natl Acad Sci USA 89:4285-4289 1992; Presta et al., Cancer Res 57:4593-4599 1997).

Selection of Additional Conservative Amino Acids for Maintaining Transplantation of CDR Site Transplantation and Affinity of Wild Type Mouse Antibodies As mentioned earlier, since the humanized antibodies constructed by simple CDR transplantation method often occasionally decrease in function when compared to wild-type non-human derived antibodies, humanization of the EC2-C peptides antigens was proceed with two clones, a clone (hEC2-C-1) transplanted with simply CDR to decrease the immunogenicity problem and a clone (hEC2-C-2) additionally reverse-substituting the amino acids located in the Vernier zone which is located in the framework of the antibody and can affect the CDR loop structure, simultaneously CDR transplantation. In the Vernier region, there are 30 amino acids, 16 in the variable heavy chain region, and 14 in the variable light chain region. Through the sequence analysis between the wild type mouse antibodies and the selected VH3-Vk1 human antibodies framework subtypes, it was confirmed that nine (28, 29, 30, 48, 49, 67, 71, 73, and 93) in the variable heavy chain region and two (49, 66) amino acids in the variable light chain region of the amino acid sequences of the Vernier region were different (See FIG. 9). In particular, the four 26-30 amino acids in the variable heavy chain region play an important role in maintaining the canonical structure through interactions in CDR1 and CDR2 in the literature (Foote J, et al., J Mol Biol., 224 (2): 487-99, 1992). Therefore, it is preferable to use the sequence of existing mouse antibody, since it is expected to stabilize the structures of CDRs of transplanted wild type antibody Amino acid 71 in the variable region of the heavy chain also plays an important role in determining the location of CDR1 and 2, and thus, nature of the CDR is determined according to whether any one of amino acids having residues with a large volume (lysine or arginine) or amino acids having residues with a small volume (valine, alanine) is located. Wild-type mouse antibody had arginine at position 71 in the heavy chain, which had a property opposed to alanine at position 71 in the human VH3 subtype framework and thus was revere-substituted.

The base and amino acid sequences of the human VH3-Vk1 subtype for sequence analysis were those of commercialized antibodies, Herceptin, with a framework of the above subtype and no significant problems in immunogenicity or expression amount.

In addition to the Vernier zone, the VH/VL interface amino acids affecting the stability are regions that affect the overall stability of the antibodies by stabilizing the binding of the variable heavy and light chain sites, since the residues thereof are directed to the interior rather than to the surface of the antibodies, and thus, for these reason, most antibodies are made up of identical amino acid residues. In the case of the above antibodies, the amino acid residues of the existing mouse antibody and human antibody were confirmed to be identical, and it was considered that they would not have a great influence upon humanization, so that no modification was made.

The nucleotide sequence and amino acid sequence of the heavy chain variable region of the constructed anti-hTM4SF5EC2-C humanized antibodies are shown in SEQ ID NOs: 20 and 16, respectively, and the nucleotide sequence and amino acid sequence of the light chain variable region are shown in SEQ ID NOs: 22 and 18, respectively. The clones for constructing the above humanized antibodies were analyzed amino acid sequences as well as structural data analysis through computer modeling. First, the variable region sequence of candidate clones and wild-type mouse antibodies primarily obtained through amino acid sequence analysis were input on an online server (URL: http://rosie.rosettacommons.org/; Lyskov S et al., PLosOne, (5): e63906, 2013), respectively, to obtain predicted structures. Each structure obtained was superimposed using Pymol software which can view the structure of the protein to observe structural changes in the CDR loop. FIG. 10 shows the structure. It was confirmed that the six CDRs transplanted on the superimposed structure did not deviate greatly when compared with the CDRs of the wild-type mouse antibody, and especially, it was confirmed that the direction of the amino acid residues in the CDR loop, which can affect the antigen binding, was mostly coincided.

Example 16

Construction and Expression of Humanized hEC2-C Antibody

To obtain humanized IgG1 Ab with intact IgG format, VH and Vk coding genes were synthesized to contain restriction enzyme sites at both the 5' and 3' ends (Bioneer, Korea). These genes were inserted into a modified pcDNA 3.4 expression vector (Invitrogen) carrying human IgG1 constant site (CH1-hinge-CH2-CH3) or human kappa chain constant site (CL) for mammalian cell expression in HEK 293F cells. The humanized EC2-C mAb was produced with HEK 293F expression system as described on Choi H J, Kim Y J, Lee S, Kim Y S. Mol Cancer Ther. 2013; 12 (12): 2748-2759 and Choi D K, Bae J, Shin S M, Shin J Y, Kim S, Kim Y S. MAbs. 2014; 6 (6): 1402-1414, and cultured for 5-7 days, and then purified using Protein A affinity chromatography according to the manufacturer's protocol. Mouse parental and humanized antibodies were evaluated for their purity by SDS-PAGE analysis.

Example 17

Production of IgG-Type Humanized Antibody Gene

The base sequence of designed humanized antibodies follows the base sequence of the commercialized high yield therapeutic antibody, Herceptin, but the other parts were converted into the base sequences upon considering the frequency of use of the codons (Sequences of Proteins of Immunological Interest, US Dept. Health and Human Services, 1991), and then a base sequence encoding the amino acid sequence of the heavy chain variable region and the light chain variable region of humanized antibodies was designed. The designed sequences were synthesized by introducing restriction enzyme recognition sequences for cloning into animal cell expression vectors at both 5' and 3' ends (Bioneer, Korea). The synthesized gene could be in the state cloned into the basic vector, pBHA vector, provided by Bioneer Co., and in order to express it in the complete IgG form, it was cloned using a restriction enzyme recognition sequence which was introduced into an animal expression vector containing a heavy chain constant region and a light chain constant region, respectively, at the time of synthesis. At this time, the amino acid and base sequence of the constant region of the heavy chain and the light chain likewise follow the nucleotide sequence of the therapeutic antibody, Herceptin.

Expression 18: Expression and Purification of Antibody

Expression of the constructed anti-hTM4SF5EC2-C humanized antibodies was performed by transient transfecting a mixture of light chain, heavy chain expression vector and polyethylenimine (PEI) (Polyscience) into HEK293-F cells (Invitrogen) and culturing it in a shaking flask with serum-free FreeStyle 293 expression medium (Invitrogen). The detailed process is as follows:

At 200 mL transfection in shaking flasks (Corning), HEK293-F cells were seeded in 100 ml medium at a density of $2.0 \times 10^6$ cells/ml and cultured at 150 rpm, 8% $CO_2$. The resulting heavy and light chain plasmids were diluted to a total of 250 μg (2.5 μg/ml) with 125 μg heavy chain and 125 μg light chain in 10 ml FreeStyle 293 expression medium (Invitrogen) to produce each humanized antibody, 750 μg PEI (7.5 μg/ml) were mixed with 10 ml of the diluted medium to make them react at room temperature for 10 minutes.

Then, the reacted mixing medium was added to 100 ml of seeded cells and cultured for 4 hours at 150 rpm and 8% $CO^2$, and then, the remaining 100 ml of FreeStyle 293 expression medium was added and cultured for 5 days to 7 days, and finally the protein produced by the cell, that is, the humanized antibody in IgG form, was secreted outside the cell by the cell and accumulated in the medium. Due to this, the humanized antibody was purified using Protein A Sepharose column (GE healthcare) from the cell culture supernatant obtained by centrifuging at 2500 rpm for 20 minutes. At this time, the purification method referred to the standard protocol provided by Protein A column company, the purified protein was measured by absorbance at 562 nm wavelength using a solution in BCA protein assay kit (Thermo) and quantified for the amounts according to the standard curve. The size and purity of the purified antibody were analyzed by reductive SDS-PAGE. As shown in FIG. 11, it was identified that the anti-mEC2-C humanized antibody of the present invention, hEC2-C-2 IgG, had a molecular weight of about 150 kDa and were purified to a purity of 99% or more.

Example 19

Confocal Image

To identify the effect of humanized anti-TM4SF5 antibody on E-cadherin and β-catenin expression, CT-26 cells and HCT-116 cells were cultured and treated with control IgG or humanized anti-TM4SF5 antibodies (10 ug/ml). After 3 days, expression of E-cadherin and β-catenin in the cells was analyzed according to Kim Y E, Kwon S, Wu G, Kim D, Park B K, Park J A, Choi K C, Kim D S, Kwon H J, Lee Y. Oncotarget. 2014; 5(18):8402-8415.

Example 20

In Vitro Cell Migration Assay

A trans-well chamber (Corning Costar) with 8 μm pores was used for the analysis. For migration analysis, the lower side of the trans-well chamber membrane was coated with 10 μg/ml of gelatin. The colonic cells ($1 \times 10^5$ cells/ml) were suspended in serum-free medium containing human IgG control or humanized anti-TM4SF5 antibodies (hEC2-C-2 Ab), and dispensed at the top of the trans-well. RPMI medium containing 10% FBS was placed in the lower chamber. Cells migrating through the pore were placed on the lower surface of the filter, fixed after 24 hours, stained with crystal violet for 30 minutes, and then the number of cells was counted with a microscope (Eclipse E-200, Nikon).

Example 21

In Vitro Wound-Healing Analysis

For wound healing analysis, $1 \times 10^6$ cells (Huh-7, and CT-26) were dispensed into 6-well plates, incubated overnight in serum-containing medium, and wounded into a single layer using a pipette tip. PBS, human IgG control, or humanized anti-TM4SF5 antibody (hEC2-C-2 Ab) (10 ug/ml) was added to the medium. At the indicated time points, the cells were fixed with 4% paraformaldehyde for 30 minutes and stained with hematoxylin for 30 minutes. The number of cells transferred to the wound site was counted in three wells per experiment treatment and three wounds per each well.

Example 22

Liver Cancer Mouse Model $5 \times 10^6$ Huh-7 cells containing 50% BD biosciences were subcutaneously injected into the dorsal right flank of 12

BALB/cAnNCri-nu/nu mice. When the tumor diameter reached 5 mm, the mice were randomly sorted into two treatment groups (6 mice/each group) of PBS and humanized anti-TM4SF5 antibody (hEC2-C-2 Ab). Antibody (25 mg/kg) were injected into the tail vein twice a week. Tumor diameters were measured at intervals of 4 days for 44 days after the injection of cancer cells, and the tumor volume was calculated according to the equation of width$^2$×length/2. BALB/cAnNCri-nu/nu mice were sacrificed when tumor size reached 2000 mm$^3$; and tumor weights were measured.

Example 23

Colon Cancer Mouse Models for Humanized Anti-TM4SF5 Antibodies (Xenotransplantation)

Twelve BALB/cAnNCri-nu/nu mice were subcutaneously injected with 5×10$^6$ HT-29 cells containing 50% BD biosciences on the dorsal right flank. When the tumor diameter reached 5 mm, the mice were randomly sorted into two treatment groups (6 mice/each group) of PBS and humanized anti-TM4SF5 monoclonal antibody (mEC2-C). Antibody (25 mg/kg) were injected into the tail vein twice a week. Tumor diameters were measured at intervals of 3 or 4 days for 30 days after the injection of cancer cells, and the tumor volume was calculated according to the equation of width$^2$×length/2. BALB/cAnNCri-nu/nu mice were sacrificed when tumor size reached 800 mm$^3$; and tumor weights were measured.

Example 24

Evaluation of Humanized Anti-TM4SF5 Antibodies as Anti-Metastatic Agents in a Lung Metastasis Model of Colorectal Cancer BALB/c mice were injected into the tail vein with 1×10$^5$ cells of mouse CT-26 colon cancer cell line (PBS control n=8, colorectal cancer cells n=36). On day 1, the cancer cell injected mice were divided into three treatment groups (n=12/each group) such as PBS, human IgG control and humanized anti-TM4SF5 antibody (hEC2-C-2 Ab). Antibody (25 mg/kg) was injected into the tail vein twice a week and body weights were measured at 2-day intervals. Survival of the mice was monitored for up to 22 days (FIG. 16).

Another experiment with the same settings was prepared to investigate the status of the lungs (n=12/each group). On day 19, the mice were sacrificed and the lungs were weighed (FIG. 17).

Example 25

Histology

For histopathological examination, tumors and lungs were removed, fixed overnight in 4% formalin solution, embedded in paraffin, and cut into 5 5 μm thick sections. The deparaffinized sections were stained with H&E (hematoxylin and eosin). Samples were then counter-stained with hematoxylin and all images were examined using a Nikon Eclipse E-200 microscope (Nikon).

The results of the above example are as follows.

Immunization with TM4SF5 Peptide Vaccine and Production of Antibodies Specific to Cyclic Peptides of TM4SF5 (FIG. 1)

To obtain antibodies that recognize structural epitopes while maintaining tight binding, the inventors have designed a structural motif of cyclic peptides that mimic TM4SF5 extracellular domain 2 (EC2). As shown in FIGS. 1A and 1B, the present inventors produced mutant peptides hTM4SF5EC2 by replacing glycine 133 and valine 156 with cysteine. Through chemical modification of peptides, we have produced cyclic peptide hTM4SF5EC2-C with disulfide bonds between the cysteine residues. We immunized mice with a liposome complex (Lipoplex (O)) containing phosphatidyl-β-oleoyl-γ-palmitoyl ethanolamine (DOPE): cholesterol hemisuccinate (CHEMS) co-encapsulated with hTM4SF5EC2-C peptides and CpG-DNA, and after the third boosting, the production of antibodies recognizing hTM4SF5EC2-C cyclic peptides was confirmed (FIG. 1C). The antibodies cross-reacted with the corresponding mouse cyclic peptides (mTM4SF5EC2-C) and their activity against linear peptides such as hTM4SF5EC2 and mTM4SF5EC2 was lower than that of cyclic peptides. The antibodies did not recognize hTM4SF5R2-3 or the corresponding epitope, mTM4SF52-3 of the mouse, suggesting that the produced antibodies recognize a conformational epitope. As shown in FIG. 1D, the produced antibodies were mainly IgG2a.

Inhibition of Growth of Colon Tumors by Immunization with M4SF5 Peptide Vaccine in Mouse Lung Metastasis Model (FIGS. 2 and 3)

To evaluate the importance of TM4SF5 as a target to control the metastasis of colon cancer in mice, the inventors first immunized BALB/c mice with TM4SF5 peptide vaccine consisting of cyclic TM4SF5 peptides (hTM4SF5EC2-C) and Lipoplex (O). Then, the effect of the TM4SF5 peptide vaccine was determined on the growth of pulmonary tumors induced by injection of CT-26 cells (FIG. 2A). CT-26 cell injected mice lost weight after 12 days of cell injection. However, mice immunized with the TM4SF5 peptide vaccine showed a pattern similar to untreated control mice (FIG. 2B). Survival of the mice was significantly increased by the peptide vaccine (80% fold to 0% on day 52) as compared to the PBS control, as shown in FIG. 2C. Immunization with the CpG-DNA-liposome complex (Lipoplex (O)) without peptides induced a partial protective effect (27% on day 52) due to nonspecific immunomodulatory effects. Using tumor volume and weight, the inventors observed that immunization with peptide vaccine reduced progression of metastatic lung tumors compared to PBS or Lipoplex (O) control (FIG. 2D-2E). Histologic examination showed that the lung tissue of appropriately vaccinated mice had a shape similar to that of normal mice (FIG. 2F). In order to confirm the anti-metastatic effect of the peptide vaccine, the inventors repeated similar experiments and checked the metastatic nodules in the lungs Immunization with peptide vaccine significantly reduced the number of pulmonary nodules compared to PBS control (FIG. 3). These results suggest that immunization with the TM4SF5 peptide vaccine may reduce the lung metastasis of colon tumors in the mouse syngeneic model.

Generation of Monoclonal Antibodies Specific to TM4SF5 Cyclic Peptides

The titration curves of the antibodies against cyclic TM4SF5 peptides (hTM4SF5EC2-C) in mouse serum were obtained by ELISA after four immunizations with liposome complex containing DOPE:CHEMS co-encapsulating hTM4SF5EC2-C peptides and CpG-DNA. (FIG. 4A). Three days after the final booster, the spleen with the highest antibody titer (hTM4SF5EC2-C) was obtained and the spleen cells fused with SP2/0 myeloma cells via conventional hybridoma technology. After 14 days, the supernatant was analyzed by ELISA method to screen for hybridoma cells secreting specific antibodies to hTM4SF5EC2-C peptides. Through the screening process, the present inventors isolated a hybridoma cell (1H1) reacting with hTM4SF5EC2-C peptides. (FIGS. 4B and 4C). The inventors performed Western blot analysis using HEK293F-TM4SF4 cells overexpressing TM4SF5 and demonstrated that the antibodies recognize the recombinant TM4SF5 protein (FIG. 4D).

The hybridoma cells were subjected to subcloning by the limiting dilution method to analyze the production of monoclonal antibodies (FIGS. 5A and 5B). Four hybridomas clones (four 1H1 derivatives) were selected and Western blot analysis was performed using HEK293F-TM4SF4 cells overexpressing TM4SF5 and proved that the antibody recognizes the recombinant TM4SF5 protein (FIG. 5D). In conclusion, a hybridoma clone (2A10) was selected for the production of monoclonal antibodies (mEC2-C) (FIG. 5D).

Property of Monoclonal Antibodies Specific for TM4SF5 Cyclic Peptides

The inventors successfully screened hybridoma cell line (2A10) and successfully isolated monoclonal antibodies that recognize hTM4SF5EC2-C peptides. Anti-TM4SF5 monoclonal antibodies (mEC2-C) were purified from multiple liquids by protein A column chromatography and their purity was determined to be 99% or more (FIG. 6A). The inventors have found that the resulting monoclonal antibodies are IgG3 (FIG. 6B). The inventors named the monoclonal antibodies as mEC2-C and confirmed its specific binding to the cyclic peptides hTM4SF5EC2-C by ELISA (FIG. 6C). As shown in FIG. 6D, binding affinities of antibodies to hTM4SF5EC2-C peptides were measured by surface plasmon resonance (SPR) analysis. The equilibrium dissociation constant (Kd) of the antibody was ~0.48 nM. The off rate (kd) of the antibodies was $10^{-5}$/sec. Thus, the present inventors have concluded that these antibodies may be more useful in clinical applications. The inventors performed immunoprecipitation and Western blot using HEK293F-TM4SF4 cells over-expressing TM4SF5 and HEK293F control cells, and demonstrated that the antibodies recognize Myc-tagged recombinant TM4SF5 protein (FIG. 6E).

Anti-TM4SF5 Monoclonal Antibodies (mEC2-C) Inhibit the Growth of Colon Cancer in a Xenograft Mouse Model The inventors observed the effect of TM4SF5-targeted monoclonal antibodies on the growth of in vivo colon cancer cells using a xenograft mouse model. First, the inventors injected HT-29 cells subcutaneously on the back of the nude mice to grow tumors. When the tumor size reached a diameter of 5 mm, the inventors injected anti-TM4SF5 monoclonal antibodies (mEC2-C) into the tail vein twice a week. Based on tumor volume and weight, anti-TM4SF5 monoclonal antibody (mEC2-C) attenuated progression of colon cancer compared to PBS control (FIG. 7B-D). The antibody treatment had no effect on body weight during the experiment (FIG. 7E). Analysis of xenotransplantation experiments showed that anti-TM4SF5 monoclonal antibody targeting colonic tumor cells could reduce tumor growth in in vivo.

Cloning of Variable Domains of Anti-TM4SF5 Monoclonal Antibody

CDNA sequences encoding the heavy and light chain variable domains ($V_H$ and $V_L$) were cloned from hybridoma cells (mEC2-C) producing anti-TM4SF5 monoclonal antibodies using conventional heavy and light chain primers. Sequences identified by DNA sequencing are shown in FIG. 8. The sequences were analyzed for known sequences and homologues using the IgBLAST program (Ye J, Ma N, Madden T L, Ostell J M. IgBLAST: Nucleic Acids Res. 2013; 41 (Web Server issue):W34-40).

Production and Property of Humanized Monoclonal Antibodies

For the clinical application of monoclonal antibodies, the antibodies should be humanized to reduce immunogenicity in humans Therefore, the present inventors analyzed immunoglobulin variable domain sequences of the obtained monoclonal antibodies mEC2-C using the IgBLAST program (Ye J, Ma N, Madden T L, Ostell J M. IgBLAST: Nucleic Acids Res. 2013; 41 (Web Server issue):W34-40), and found that the variable domain subtype belongs to mouse VH2-Vk8. For the humanization of mEC2-C mAb, the inventors have found that the VH3-Vk1 framework was selected by referring to the fact that the framework is most commonly observed in the human germ line repertoire (Caravella J A, Wang D, Glaser S M, Lugovskoy A. Curr Comput Aided Drug Des. 2010; 6 (2): 128-138). The inventors have grafted some framework sequences, in this case, Herceptin framework and CDR region into VH3-Vk1 framework in a well-established manner (Kabat E A, Wu T T. J Immunol. 1991; 147(5):1709-1719). The structures derived from mEC2-2 and humanized monoclonal antibody (hEC2-C-2) were modeled and compared, indicating that they are not identical to each other, but are similar to each other (FIGS. 9 and 10). The inventors generated recombinant humanized monoclonal antibody (hEC2-C-2) using HEK 293F cells (FIG. 11A) and assessed its reactivity (FIG. 11B-D). The humanized antibody specifically responded to cyclic peptides hTM4SF5EC2-C based on ELISA, but not hTM4SF5R2-3 (FIG. 11B). The equilibrium dissociation constant (Kd) of the antibody was ~22.7 pM, which was about 20-fold lower than the original mouse monoclonal antibody mEC2-C (FIG. 11C). The humanized antibody was able to detect TM4SF5 protein in HEK 293F cells overexpressing TM4SF5 based on Western blot and immunoprecipitation analysis (FIG. 11D).

Therefore, the present inventors can conclude that the humanized antibody is fully responsive to the TM4SF5 protein and has a higher affinity compared to the original monoclonal antibody.

Effects of Humanized Anti-TM4SF5 Antibodies on β-Catenin Expression and Migration of Colon Cancer Cells TM4SF5 activates integrin-mediated signaling pathways critical for tumor cell metastasis and cell migration/invasion (Lee S A, Kim T Y, Kwak T K, Kim H, Kim S, Lee H J, Kim S H, Park K H, Kim H J, Cho M, Lee J W. J Cell Biochem. 2010; 111(1):59-66; Jung O, Choi S, Jang S B, Lee S A, Lim S T, Choi Y J, Kim H J, Kim D H, Kwak T K, Kim H, Kang M, Lee M S, Park S Y, et al. J Cell Sci. 2012; 125 (Pt 24):5960-5973). Therefore, the inventors evaluated the in vitro effect of humanized anti-TM4SF5 antibody on cell migration using CT-26 cells and HCT-116 cells. As shown in FIG. 12A, the inventors have shown that the addition of humanized anti-TM4SF5 antibody inhibited the migration of CT-26 cells, but not PBS or human IgG. In contrast, the antibody was ineffective for migration of HCT-116 cells that did not express TM4SF5. The present inventors also performed wound healing assays in vitro. As shown in FIG. 12B, the migration of CT-26 cells to the injured site was greatly inhibited compared to the PBS or human IgG control group, but there was no difference among PBS, human IgG control, or anti-TM4SF5 on the wound healing ability in HCT-116 cells.

In order to examine the effect of anti-TM4SF5 antibody on the cell interaction characteristics, the inventors checked the expression of E-cadherin and β-catenin in CT-26 cells and HCT-116 cells (FIG. 13). Confocal image data showed β-catenin expression was significantly increased against humanized anti-TM4SF5 antibody in CT-26 cells (FIG. 13A). Expression of E-cadherin was not observed in CT-26 cells despite the treatment, suggesting that the basal expression of E-cadherin is very low in CT-26 cells. In contrast, the expression of E-cadherin and β-catenin was unchanged in HCT-116 cells after treatment with humanized anti-TM4SF5 antibody. Western blot analysis showed the same results (FIG. 13B). Thus, humanized anti-TM4SF5 antibody reduces mobility and increase cell-cell interactions in TM4SF5 expressing cells.

Humanized Anti-TM4SF5 Antibody Inhibits HCC Tumor Growth in a Xenograft Mouse Model The inventors investigated the effect of TM4SF5-targeted humanized antibody on the growth of HCC cells using a xenograft mouse model. First, the inventors injected Huh-7 cells subcutaneously into the back of the mouse to grow tumors. When the tumor size reached a diameter of 5 mm, the inventors administered PBS or humanized anti-TM4SF5 antibody to the tail vein twice a week. According to tumor volume and weight, humanized anti-TM4SF5 antibody attenuated the progression of HCC tumors when compared to PBS controls (FIG. 14B-E). Analysis of xenotransplantation experiments showed that humanized anti-TM4SF5 antibody targeting HCC tumor cells were sufficient to reduce tumor growth in in vivo.

Humanized Anti-TM4SF5 Antibody Inhibit Colon Cancer Growth in Xenotransplantation Mouse Models The inventors observed the effect of TM4SF5-targeted humanized antibody on the growth of in vivo colon cancer cells using a xenograft mouse model. First, the inventors injected HT-29 cells subcutaneously on the back of the nude mice to grow tumors. When the tumor size reached a diameter of 5 mm, the inventors administered PBS or humanized anti-TM4SF5 antibody twice a week into the tail vein. According to tumor volume and weight, humanized anti-TM4SF5 antibody attenuated the progression of colon tumors compared to PBS controls (FIG. 15B-D). The antibodies treatment had no effect on body weight during the experiment (FIG. 15E). Analysis of xenotransplantation experiments showed that humanized anti-TM4SF5 antibody targeting colorectal cancer could reduce tumor growth in in vivo.

Humanized Anti-TM4SF5 Antibody Inhibits the Growth of Colon Tumors in the Mouse Lung Metastasis Model It can be hypothesized that an immunization-induced TM4SF5-specific antibody directly contributes to the anti-metastatic effect, since immunization of mice with the TM4SF5 peptide vaccine inhibits the growth of lung tumor tissue by injection of CT-26 cells.

Thus, we next examined the effect of humanized anti-TM4SF5 antibody on lung metastasis according to the experimental schedule as shown in FIG. 16A. One day after the injection of CT-26 cells, the inventors injected normal IgG or humanized antibody hEC2-C-2 into the tail vein and checked the effect of the antibodies in mice. The control mouse lost its weight approximately 16 days after the injection of CT-26 cell. However, mice injected with humanized antibody hEC2-C-2 showed body weights similar to untreated control mice (FIG. 16B). Survival of mice was greatly increased by humanized anti-TM4SF5 antibody as compared to human IgG control (75% vs. 0%), as shown in FIG. 16C.

In order to confirm the anti-metastatic effect of humanized anti-TM4SF5 antibody, the inventors repeated similar experiments and checked lung metastasis. Mice injected with humanized antibody hEC2-C-2 significantly reduced the formation and growth of pulmonary metastatic tumors compared to PBS controls (FIG. 17). Taking changes in tumor volume and weight into consideration, anti-TM4SF5 antibody reduced the growth of lung metastasis tumors compared to human IgG (FIG. 17B-D). Thus, the present inventors can obtain the conclusion that the humanized anti-TM4SF5 monoclonal antibody can alleviate lung metastasis of colon tumors in a mouse syngeneic model.

The invention claimed is:

1. The antibody against peptides, said peptides comprising an amino acid sequence selected from the group consisting of SEQ ID NOS: 1 and 2 or peptides comprising an amino acid sequence selected from the group consisting of cyclic peptides linked by a disulfide bond between the 3rd cysteine amino acid and the 26th cysteine amino acid in sequences of SEQ ID NO: 1 or SEQ ID NO: 2, wherein said antibody comprises a heavy chain variable region having a heavy chain complementarity determining region (CDR) amino acid sequence of CDRH1 consisting of the sequence of SEQ ID NO: 3 or SEQ ID NO: 4 of the sequence listing, CDRH2 consisting of the sequence of SEQ ID NO: 5 or SEQ ID NO: 6 of the sequence listing, and CDRH3 consisting of the sequence of SEQ ID NO: 7 or SEQ ID NO: 8 of the sequence listing; and a light chain variable region having a light chain CDR amino acid sequence of CDRL1 consisting of the sequence of SEQ ID NO: 9 or SEQ ID NO: 10 of the sequence listing, CDRL2 consisting of SEQ ID NO: 11 or SEQ ID NO: 12 of the sequence listing and CDRL3 consisting of SEQ ID NO: 13 or SEQ ID NO: 14.

2. The antibody according to claim 1, characterized in that the heavy chain variable region has the amino acid sequence of SEQ ID NO:15 or SEQ ID NO:16.

3. The antibody according to claim 1, characterized in that the light chain variable region has the amino acid sequence of SEQ ID NO:17 or SEQ ID NO:18.

* * * * *